(12) United States Patent
Garzino-Demo et al.

(10) Patent No.: US 6,569,418 B1
(45) Date of Patent: May 27, 2003

(54) IMMUNO-MODULATING EFFECTS OF CHEMOKINES IN DNA VACCINATION

(75) Inventors: Alfredo Garzino-Demo, Baltimore, MD (US); Anthony L. DeVico, Alexandria, VA (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 0 days.

(21) Appl. No.: 09/591,992

(22) Filed: Jun. 12, 2000

Related U.S. Application Data

(60) Provisional application No. 60/069,281, filed on Dec. 11, 1997, and provisional application No. 60/186,416, filed on Mar. 2, 2000.

(51) Int. Cl.[7] .......................... A61K 45/05; A61K 5/68; A61K 39/21; C12P 21/02; C07K 4/12
(52) U.S. Cl. .................... 424/85.1; 424/204.1; 424/9.1; 424/205.1; 424/208.1; 424/278.1; 424/199.1; 514/44; 530/351; 530/402; 435/5; 435/6; 435/69.5
(58) Field of Search .......................... 424/204.1, 208.1, 424/278.1, 199.1, 85.1, 9.1, 205; 530/351, 395, 402; 435/5, 6, 69.5; 514/44

(56) References Cited

PUBLICATIONS

Cox et al. Vaccine 1997, vol. 15, pp. 248–256, especially see the Table 2 on p. 251.*
Godiska ey t al. J. Exp. Med. May 1997, vol. 185, pp. 1595–1604.*
Xiang et al. Immunology and Cell Biology Apr. 1997, vol. 75, pp. 397–401.*
Fulginity al. JAMA 1967, vol. 202, pp. 101–106.*
Prince et al. J. Virol. 1986, vol. 57, pp. 721–728.*
Girard Cancer Detection and Prevention 1990, vol. 14, pp. 411–413.*
Barouch et al. Nature 2002, vol. 415, pp. 335–339.*
Donnelly et al. Annu. Rev. Immune. 1997, vol. 15, pp. 617–648.*
Poignard et al. Immunity 1999, vol. 10, pp. 431–438.*

* cited by examiner

*Primary Examiner*—James Housel
*Assistant Examiner*—Bao Qun Li
(74) *Attorney, Agent, or Firm*—Marianne Fuierer; Steven J. Hultquist; Yongzhi Yang

(57) ABSTRACT

The present invention relates to a composition and method for enhancing the efficacy of a vaccine in a subject treated with the vaccine by administering to the subject an antigen in conjunction with a chemokine.

6 Claims, 15 Drawing Sheets

Figure 2A:
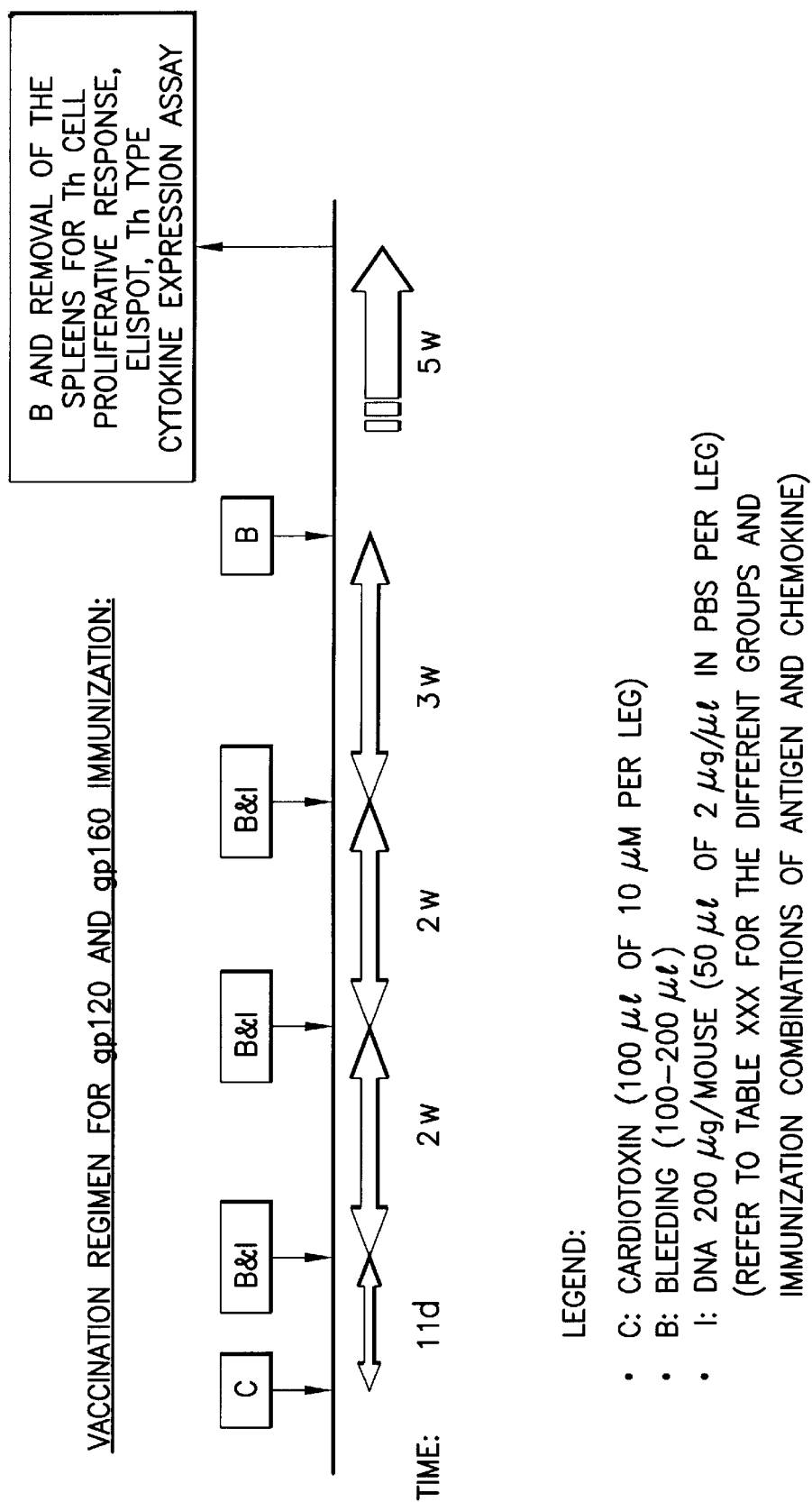

```
GAGACATACA GGACAGAGC ATG GCT CGC CTA CAG ACT GCA CTC CTG GTT GTC    52
                    Met Ala Arg Leu Gln Thr Ala Leu Leu Val Val
                    -24                      -20              -15

CTC GTC CTC CTT GCT GTG GCG CTT CAA GCA ACT GAG GCA GGC CCC TAC    100
Leu Val Leu Leu Ala Val Ala Leu Gln Ala Thr Glu Ala Gly Pro Tyr
            -10                  -5                       1

GGC GCC AAC ATG GAA GAC AGC GTC TGC TGC CGT GAT TAC GTC CGT TAC    148
Gly Ala Asn Met Glu Asp Ser Val Cys Cys Arg Asp Tyr Val Arg Tyr
        5                   10                  15

CGT CTG CCC CTG CGC GTG GTG AAA CAC TTC TAC TGG ACC TCA GAC TCC    196
Arg Leu Pro Leu Arg Val Val Lys His Phe Tyr Trp Thr Ser Asp Ser
            20                  25                  30        35

TGC CCG AGG CCT GGC GTG GTG TTG CTA ACC TTC AGG GAT AAG GAG ATC    244
Cys Pro Arg Pro Gly Val Val Leu Leu Thr Phe Arg Asp Lys Glu Ile
        40                  45                  50

TGT GCC GAT CCC AGA GTG CCC TGG GTG AAG ATG ATT CTC AAT AAG CTG    292
Cys Ala Asp Pro Arg Val Pro Trp Val Lys Met Ile Leu Asn Lys Leu
        55                  60                  65
```

FIG.1A-1

| | | | | |
|---|---|---|---|---|
| AGC CAA TGAAGAGCCT ACTCTGATGA CCGTGGCCCTT GGCTCCTCCA GGAAGGCTCA | | | | 348 |
| Ser Gln | | | | |

| | | | | | |
|---|---|---|---|---|---|
| GGAGCCCTAC | CTCCCTGCCA | TTATAGCTGC | TCCCCGCCAG | AAGCCTGTGC | CAACTCTCTG | 408
| CATTCCCTGA | TCTCCATCCC | TGTGGCTGTC | ACCCTTGGTC | ACCTCCGTGC | TGTCACTGCC | 468
| ATCTCCCCCC | TGACCCCTCT | AACCCATCCT | CTGCCTCCCT | CCCTGCAGTC | AGAGGGTCCT | 528
| GTTCCCATCA | GCGATTCCCC | TGCTTAAACC | CTTCCATGAC | TCCCCACTGC | CCTAAGCTGA | 588
| GGTCAGTCTC | CCAAGCCTGG | CATGTGGCCC | TCTGGATCTG | GGTTCCATCT | CTGTCTCCAG | 648
| CCTGCCCACT | TCCCTTCATG | AATGTTGGGT | TCTAGCTCCC | TGTTCTCCAA | ACCCATACTA | 708
| CACATCCCAC | TTCTGGGTCT | TTGCCTGGGA | TGTTGCTGAC | ACTCAGAAAG | TCCCACCACC | 768
| TGCACATGTG | TAGCCCCACC | AGCCCCTCCAA | GGCATTGCTC | GCCCAAGCAG | CTGGTAATTC | 828
| CATTTCATGT | ATTAGATGTC | CCCTGGCCCT | CTGTCCCCTC | TTAATAACCC | TAGTCACAGT | 888
| CTCCGCAGAT | TCTTGGGATT | TGGGGGTTTT | CTCCCCCACC | TCTCCACTAG | TTGGACCAAG | 948

FIG.1A-2

```
GTTTCTAGCT AAGTTACTCT AGTCTCCAAG CCTCTAGCAT AGAGCACTGC AGACAGGCCC    1008
TGGCTCAGAA TCAGAGCCCA GAAAGTGGCT GCAGACAAAA TCAATAAAAC TAATGTCCCT    1068
CCCCTCTCCC TGCCAAAAGG CAGTTACATA TCAATACAGA GACTCAAGGT CACTAGAAAT    1128
GGGCCAGCTG GGTCAATGTG AAGCCCCAAA TTTGCCCAGA TTCACCTTTC TTCCCCCACT    1188
CCCTTTTTTT TTTTTTTTTT TTTGAGATGG AGTTTCGCTC TTGTCACCCA CGCTGGAGTG    1248
CAATGGTGTG GTCTTGGCTT ATTGAAGCCT CTGCCTCCTG GGTTCAAGTG ATTCTCTTGC    1308
CTCAGCCTCC TGAGTAGCTG GGATTACAGG TTCCTGCTAC CACGCCCAGC TAATTTTTGT    1368
ATTTTTAGTA GAGACGAGGC TTCACCATGT TGGCCAGGCT GGTCTCGAAC TCCTGTCCTC    1428
AGGTAATCCG CCCACCTCAG CCTCCCAAAG TGCTGGGATT ACAGGCGTGA GCCACAGTGC    1488
CTGGCCTCTT CCCTCTCCCC ACTGCCCCCC CCAACTTTTT TTTTTTTTT ATGGCAGGGT    1548
CTCACTCTGT CGCCCAGGCT GGAGTGCAGT GGCGTGATCT CGGCTCACTA CAACCTCGAC    1608
CTCCTGGGTT CAAGTGATTC TCCCACCCCA GCCTCCCAAG TAGCTGGGAT TACAGGTGTG    1668
```

FIG.1A-3

```
TGCCACTACG GCTGGCTAAT TTTTGTATTT TTAGTAGAGA CAGGTTTCAC CATATTGGCC   1728

AGGCTGGTCT TGAACTCCTG ACCTCAAGTG ATCCACCTTC CTTGTGCTCC CAAAGTGCTG   1788

AGATTACAGG CGTGAGCTAT CACACCCAGC CTCCCCCTTT TTTTCCTAAT AGGAGACTCC   1848

TGTACCTTTC TTCGTTTTAC CTATGTGTCG TGTCTGCTTA CATTTCCTTC TCCCCTCAGG   1908

CTTTTTTTGG GTGGTCCTCC AACCTCCAAT ACCCAGGCCT GGCCTCTTCA GAGTACCCCC   1968

CATTCCACTT TCCCTGCCTC CTTCCTTAAA TAGCTGACAA TCAAATTCAT GCTATGGTGT   2028

GAAAGACTAC CTTTGACTTG GTATTATAAG CTGGAGTTAT ATATGTATTT GAAAACAGAG   2088

TAAATACTTA AGAGGCCAAA TAGATGAATG GAAGAATTTT AGGAACTGTG AGAGGGGAC   2148

AAGGTGAAGC TTTCCTGGCC CTGGGAGGAA GCTGGCTGTG GTAGCGTAGC GCTCTCTCTC   2208

TCTGTCTGTG GCAGGAGCCA AAGAGTAGGG TGTAATTGAG TGAAGGAATC CTGGGTAGAG   2268

ACCATTCTCA GGTGGTTGGG CCAGGCTAAA GACTGGGAGT TGGGTCTATC TATGCCTTTC   2328

TGGCTGATTT TTGTAGAGAC GGGGTTTTGC CATGTTACCC AGGCTGGTCT CAAACTCCTG   2388
```

FIG.1A-4

```
GGCTCAAGCG ATCCTCCTGG CTCAGCCTCC CAAAGTGCTG GGATTACAGG CGTGAATCAC    2448

TGCGCCTGGC TTCCTCTTCC TCTTGAGAAA TATTCTTTTC ATACAGCAAG TATGGGACAG    2508

CAGTGTCCCA GGTAAAGGAC ATAAATGTTA CAAGTGTCTG GTCCTTTCTG AGGGAGGCTG    2568

GTGCCGCTCT GCAGGGTATT TGAACCTGTG GAATTGGAGG AGGCCATTTC ACTCCCTGAA    2628

CCCAGCCTGA CAAATCACAG TGAGAATGTT CACCTTATAG GCTTGCTGTG GGGCTCAGGT    2688

TGAAAGTGTG GGGAGTGACA CTGCCTAGGC ATCCAGCTCA GTGTCATCCA GGGCCTGTGT    2748

CCCTCCCGAA CCCAGGGTCA ACCTGCCTGC CACAGGCACT AGAAGGACGA ATCTGCCTAC    2808

TGCCCATGAA CGGGGCCCTC AAGCGTCCTG GGATCTCCTT CTCCCTCCTG TCCTGTCCTT    2868

GCCCCTCAGG ACTGCTGGAA AATAAATCCT TTAAAATAGT AAAAAAAAAA AAAAA         2923
```

| FIG.1A-1 |
|----------|
| FIG.1A-2 |
| FIG.1A-3 |
| FIG.1A-4 |
| FIG.1A-5 |

FIG.1A

FIG.1A-5

```
Met Ala Arg Leu Gln Thr Ala Leu Leu Val Val Leu Leu Ala
-24                 -20                 -15             -10
Val Ala Leu Gln Ala Thr Glu Ala Gly Pro Tyr Gly Ala Asn Met Glu
       -5                       1                 5
Asp Ser Val Cys Cys Arg Asp Tyr Val Arg Tyr Arg Leu Pro Leu Arg
               10                  15                 20
Val Lys His Phe Tyr Tyr Trp Thr Ser Asp Ser Cys Pro Arg Pro Gly
       25                  30                 35                 40
Val Val Leu Leu Thr Phe Arg Asp Lys Glu Ile Cys Ala Asp Pro Arg
               45                  50                 55
Val Pro Trp Val Lys Met Ile Leu Asn Lys Leu Ser Gln
       60                  65
```

FIG.1B

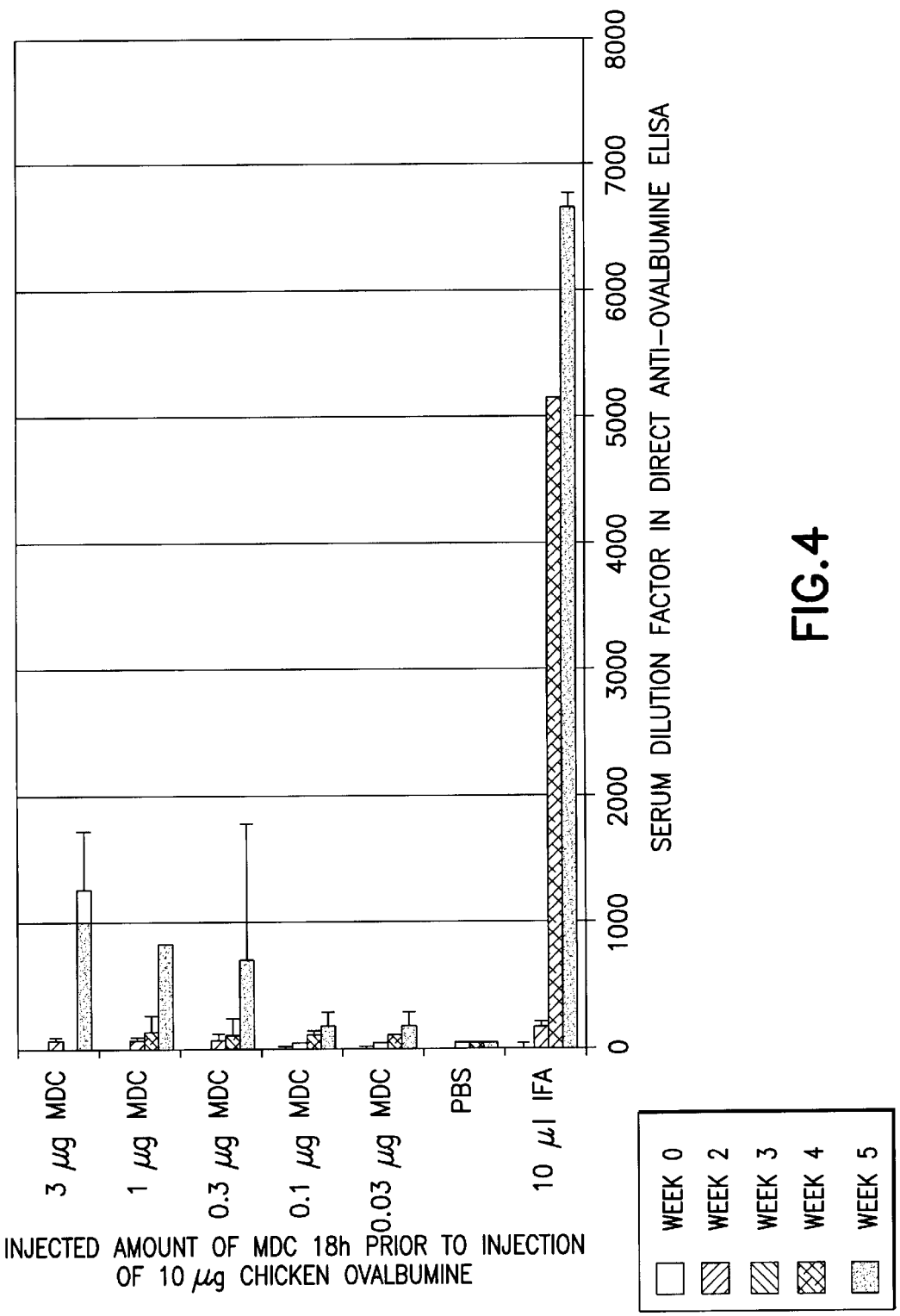

IMMUNO-MODULATING EFFECTS OF CHEMOKINES IN DNA VACCINATION

This application is a continuation and is based on and claims priorty to International Patent Application No. PCT/US98/26291, filed Dec. 11, 1998, which in turn is based on and claims priority to U.S. Prov. Patent Application No. 60/069,281 filed Dec. 11, 1997. This application is also based on and claims priority to U.S. Prov. Patent Application No. 60/186,416 filed Mar. 2, 2000.

1. FIELD OF THE INVENTION

The present invention relates to a method to enhance the efficacy of a vaccine by administration of a chemokine in conjunction with the vaccine. The present invention also relates to compositions useful in the practice of this method.

2. BACKGROUND OF THE INVENTION

DNA immunization is presently being developed as an inexpensive and safe means for providing immunizations to large numbers of people. One of the shortcomings of this approach is the relatively weak immune response triggered by DNA vaccines. The present invention provides for the administration of select chemokines to enhance the immune response to DNA vaccines.

Because of their ability to attract discrete sub-populations of leukocytes to sites of inflammation and antigen presentation, chemokines are key agents in eliciting immune responses. In addition, chemokines reportedly can influence the T helper response towards a Th1 (i.e. cell mediated) or Th2 (i.e. humoral) profile, according to the differential distribution of receptors on target cells.

Preferred chemokines according to the practice of the present invention include RANTES (regulated on activation, normal T cell expressed and secreted), a chemokine which has receptors on both Th1 and Th2 cells, MCP-1 (monocyte chemoattractant protein), which is Th1-type associated, and the Th2-type associated chemokine BLC (B lymphocyte chemoattractant) and MDC (macrophage-derived chemoattractant). The inventors have studied the immuno-modulating properties of these chemokines in conjunction with DNA immunization, using HIV-$1_{BaL}$ gp 120 and membrane-bound HIV-$1_{BaL}$ gp 160 as antigens.

The inventors have discovered that chemokines modulate immune responses according to their Th-type polarization. Accordingly, the investigated chemokines can be ranked in the following order of induction of Th-2 vs Th-1 responses: BLC (inducing mostly humoral responses), MDC, MCP-1 and RANTES (inducing mostly cellular responses). Quantitatively, MCP-1 was the strongest inducer of cellular responses, while the BLC induced the strongest humoral response.

These results are of great importance from the perspective of developing and optimizing vaccination regimens, in particular, against viral infections or cancer, but also, in general where directed or combined Th-type responses are sought.

2.1 DNA Vaccines

DNA-based vaccines combine safety, ease of use, handling and modification and cost-effective production with the efficacy and effectiveness of live-attenuated vaccines. They are capable of eliciting both strong humoral and cell-mediated immunity (Moelling, K., 1997, Donnelly, J. J. et al., 1997; Montgomery, D. L. et al., 1997). Therefore DNA immunization represents a new approach for prevention (vaccination) and treatment (immune-based therapy) of infectious and neoplastic diseases. It has been shown that many factors contribute to the outcome of the immune response (Cohen, A. D. et al., 1998; Chun, S. et al., 1998) and might therefore be exploited. The present inventors have discovered that co-administration of chemokines with DNA vaccines significantly affects the immune response, both in amplitude and quality. The chemokines used in the empirical work presented herein are representative of classes of chemokines which attract specific subsets of lymphocytes and/or antigen presenting cells.

The surprising discovery that genes in plasmid expression vectors are expressed in vivo after intramuscular (i.m.) injection and that this expression stimulates an immune response against the plasmid-encoded proteins, has led to the concept of 'DNA vaccination' (Wolff et al., 1990). It has been shown that upon plasmid injection both antigen-specific antibody (Ab) responses and cytotoxic T Cell (CTL) responses are produced (Tang, D., 1992; Wang et al., 1993; Ulmer et al., 1993), without damaging the muscular tissue. The DNA vaccination procedure is safe because it uses only a part of the genome of the pathogen, hence making an active infection impossible. The ability to express virtually any antigen, or antigen combination by genetic engineering, coupled with efficacy and safety, has fueled the great popularity of DNA vaccines.

A considerable number of studies have focused on HIV and cancer vaccines (Fomsgaard, A., 1999; Barnett, S. W. et al., 1998; Kennedy, R. C., 1997; Oppenheim, J. et al., 1996; Burton, D. R. & Moore, J. P., 1998), and phase III studies using HIV-based vaccines have already begun (VaxGen (1999). However, current DNA vaccines still need improvement, since it is likely that both strong CTL responses and high neutralizing Ab titers are required, at least for some vaccines to be effective (Corel, et al., 1998), and indeed, most of the vaccines used have only limited efficacy in inducing efficient humoral responses (AIDS Alert, 1998).

DNA immunization is generally performed using immuno-stimulants (adjuvants) (Falo, L. D. Jr. & Storkus, W. J., 1998, Sasaki, S., 1998). Those adjuvants can be of very different nature (Allison, A., 1997; Gupter, R. K. and Siber, G. R., 1995; Cox, J. C. and Coulter, A. R., 1997): currently used preparations include bacterial cell-wall derivatives (Freund's adjuvant), oil-based emulsions (MF-51, SAF-1), aluminum salts (alum), saponine derivatives (QS21), or polymers (polyphosphazene). More recently cytokines and chemokines have been proposed as "natural" adjuvants, in both DNA-based and traditional immunization protocols (Xin, K. Q., 1999; Sin, J. I. et al 1999; Wang, B. et al., 1993; Okada, E. et al., 1997).

2.2 Polypeptide Vaccines

Classical protein vaccination protocols are effective in inducing high humoral response (Sha, Z. et al., 1999), unlike, for the time being, DNA immunization. The immunization with protein also allows the establishment of an accurate dose dependency, which is not possible using DNA vaccination protocols, since in DNA vaccination the ratio of administrated and finally expressed DNA remains unknown. On the contrary, the exact amount of injected protein is known and there is no delay via the process of transcription, translation and secretion, so that when chemokines are coadministered, their potential enhancing effect on antigen presentation will occur in hours rather than days.

Protein immunization is not very effective for inducing cell-mediated immunity, due to the route of antigen processing and presentation. However, depending on the pathogen, cellular responses may be crucial (Connor, R. I. et al., 1998). Special adjuvants have been designed to circumvent this hurdle (Sheikh, N. A. et al., 1999); however, these formulations using these adjuvants have the potential disadvantage of denaturing the protein, and thereby possibly preventing the elicitation of a relevant antibody response (VanCott, T. C. et al., 1997).

Another advantage of protein immunization lies in the ability to quickly study potential B or T cell epitopes. Peptide vaccination has been shown to be promising in both T cell induction and suppression (Ruiz, P. J., 1999: Toes, R. E., 1996), which has lead to extensive studies in pharmaceutical drug design, although T cell epitopes, in contrast to B cell epitopes, would be limited to the major MHC-haplotypes that present them.

Protein vaccination is as safe as DNA vaccination since there is no risk of infection by a live pathogen. In addition, autoimmune or tolerance reactions, which might be elicited by long-term expression of plasmid-based vaccines (Mor, G., 1997), are less likely to be induced by protein immunization. Therefore, protein-DNA mixed protocols have the potential of combining the advantages of DNA and protein immunization, with the lowest risk of inducing undesired or ineffective responses (Bruehl, P. et al., 1998; Richmond, J. F. L. et al., 1998; Barnett, S. W., 1998).

2.3 Chemokines

Chemokines are a family of small cytokines, that are released in response to infection together with other inflammatory cytokines (Mackay, C. R., 1997). Their molecular masses range from 6–14 kDa (Ward, S. G., 1998), and they all have related amino acid sequences which are between 20 and 50% sequentially homologous. Chemokines are multiple mediators, but were first studied as inducers of chemotaxis of specific leukocytes (Nelson, P. I. & Krensky, E. M., 1998; Kim, C. H. et al., 1999; Moser B, 1998). Further studies have revealed that chemokines also stimulate lymphocyte development, angiogenesis, degranulation of granulocytes, respiratory bursts and the release of lysosomal enzymes in monocytes. Furthermore, chemokines were shown to reduce the threshold of responsiveness of immune cells to other inflammatory mediators (Taub, D. D., 1996). These properties render chemokines particularly important in localizing and enhancing inflammation.

Chemokines are divided into four different subfamilies, according to the position of the first two cysteines in their primary sequence: the α-chemokine subclass bears a CXC-motif, where the two cysteines (C) are separated by one amino acid; the β-chemokines contain a CC motif, the γ-subclass lacks one cysteine residue, and is yet represented only by one member, lymphotactin, and in δ-chemokines, or $CX_3C$ subclass, the two cysteines are separated by three amino-acids. These cysteine residues form disulfide bridges with two other cysteines located further downstream in the primary sequence, thus stabilizing the tertiary structure of these chemokines.

Both primary and tertiary structures are crucial in inducing differential chemoattractant responses, determining binding to specific receptors (Baggiolini, M., 1997). However, the chemokine/chemokine receptor system is in part redundant, since overlapping ligand specificity by interaction with several chemokine receptors has been shown (Campbell, J. J. et al., 1997). This relatively complicated network of ligand/receptor interaction has been tentatively explained by the "multistep navigation model" (Foxman, F. F., 1997), according to which migrating lymphocytes follow a hierarchy, of chemotactic gradients. Leukocytes will encounter and respond to multiple chemoattractant signals in a complex spatial and temporal pattern. Those signals guide the leukocytes from the vascular system to the site of inflammation by inducing sequentially their rolling through the endothelium and the firm adhesion and extravasation at the peak of the gradient, namely, where most adhesion molecules are expressed. Additional leukocytes may be directed via other signals through the tissue to the site of inflammation. During this migration, several receptors may be triggered simultaneously and/or successively on both leukocytes as on the cells involved in their 'guidance.' This model therefore proposes specific blockage sites for therapeutic purposes, such as treating allergic and autoimmune diseases, with fewer side effects than common immunosuppressants. Specific blocking of chemokine-receptors could be achieved by specific antagonists, such as monoclonal Abs or modified chemokine derivates (Simmons, G. et al., 1997; Chen, J. D., 1997; Baggliolini, M. and Moser, B., 1997; Wu, L., 1997).

Chemokine receptors are designated CXCR followed by a number when binding cc-chemokines and CCR followed by a number when binding β-chemokines. All chemokine receptors belong to the group of G-protein-coupled seven transmembrane domain receptors (Baggiolini M, 1997).

3. DETAILED DESCRIPTION OF THE INVENTION

3.1 HIV Vaccines

Human immunodeficiency virus (HIV) induces a persistent and progressive infection leading, in the vast majority of cases, to the development of the acquired immunodeficiency syndrome (AIDS) (Barre-Sinoussi et al., 1983, *Science* 220:868–870; Gallo et al., 1984, *Science* 224:500–503). The HIV envelope surface glycoproteins are synthesized as a single 160 kilodalton precursor protein, which is cleaved by a cellular protease during viral budding into two glycoproteins, gp41 and gp120. gp41 is a transmembrane glycoprotein and gp120 is an extracellular glycoprotein which remains non-covalently associated with gp41, possibly in a trimeric or multimeric form (Hammerskjold, M. and Rekosh, D., 1989, *Biochem. Biophys. Acta* 989:269–280). The V3 loop of gp120is the major determinant of sensitivity to chemokine inhibition of infection or replication (Cocchi et al., 1996, *Nature Medicine* 2:1244–1247; and Oravecz et al., 1996, *J. Immunol.* 157:1329–1332).

Although considerable effort is being directed towards the design of effective therapeutics, currently no completely curative anti-retroviral drugs against AIDS exist. The HIV-1 envelope proteins (gp160, gp120, gp41) have been shown to be the major antigens for neutralizing anti-HIV antibodies present in AIDS patients (Barin et al., 1985, *Science* 228:1094–1096). These proteins are promising antigen candidates for anti-HIV vaccines. Several groups have begun to use various portions of gp160, gp 120, and/or gp41 as immunogenic targets for the host immune system (see, for example, Ivanoff, et al., U.S. Pat. No. 5,141,867; Saith, et al., PCT publication WO 92/22654; Shafferman, A., PCT Publication WO 91/09872; Formoso, et al., PCT Publication WO 90/07119). Therefore, methods to increase the efficacy of vaccines against HIV, especially vaccines using gp120 as the antigen, are needed.

Additionally, a novel vaccine technology, designated genetic vaccination, nucleic acid vaccination or DNA vaccination, has been explored to induce immune responses in vivo. Injection of cDNA expression cassettes results in in vivo expression of the encoded proteins (Dubensky, et al., 1984, *Proc. Natl. Acad. Sci. USA* 81:7529–7533; Raz, et al., 1993, *Proc. Natl. Acad. Sci. USA* 90:4523; Wolff, et al., 1990, *Science* 247:1465–1468), with the concomitant development of specific cellular and humoral immune responses directed against the encoded antigen(s) (Wang, et al., 1995, *Hum. Gene Ther.* 6:407–418; Ulmer, et al., 1993, *Science* 259:1745–1749; Tang, et al., 1992, *Nature* 356:152–154; Michel, et al., 1995, *Proc. Natl. Acad. Sci. USA* 92:5307–5311; and Lowrie, et al., 1994, *Vaccine* 12:1537–1540). Humoral and cellular responses have been induced to HIV-1 and SIV antigens through various applications of this technology in macaques (Wang, et al., 1995, *Virology* 221:102–112; Wang, et al., 1993, *Proc. Natl. Acad. Sci. USA* 90:4156–4160; and Boyer, et al., 1996, *J. Med. Primatol.* 25:242–250) as well as mice (Wang, et al., 1995, *Virology* 221:102–112; Lu, et al., 1995, *Virology* 209:147–154; Haynes, et al., 1994, *AIDS Res. Hum. Retroviruses* 10 (Suppl. 2):S43–S45; Okuda, et al., 1995, *AIDS Res. Hum. Retroviruses* 11:933–943).

Recently, Lekutis, et al. (1997, *J. Immunol.* 158:4471–4477), assessed the TH cell response elicited by an HIV-1 gp120 DNA vaccine in rhesus monkeys by isolation of gp120-specific, MHC class II-restricted $CD4^+$ T cell lines from the vaccinated animals. Lekutis, et al. showed that the isolated cell lines proliferated in response to APC in the presence of recombinant gp120, as well as to APC expressing HIV encoded env protein. Lekutis, et al. further showed that these cell lines responded to env by secreting IFN-Γ and IFN-α without appreciable IL-4 production. These results demonstrate that the animals exhibited a cellular immune response to the DNA vaccine.

Boyer, et al. (1997, *Nature Medicine* 3:625–532), inoculated chimpanzees with an HIV-1 DNA vaccine encoding Env, Rev, and Gag/Pol, and found that the immunized animals developed specific cellular and humoral immune responses to these proteins. After challenging the immunized animals with a heterologous chimpanzee titered stock of HIV-1 SF2, Boyer, et al. further found, using a Reverse Transcriptase-Polymerase Chain Reaction (RT-PCR) assay, that those animals vaccinated with the DNA vaccine were protected against infection whereas the control animals were not so protected.

Kim, et al., (1997 *J. Immunol.* 158:816–826), investigated the role of co-delivery of genes for IL-12 and GM-CSF along with DNA vaccine formulation for HIV-1 antigens env and gag/pol in mice. Kim, et al. observed a dramatic increase in specific CTL response from the mice immunized with the HIV-1 DNA vaccine and IL-12. Kim et al. also observed that the co-delivery of IL-12 genes resulted in the reduction of specific antibody response, whereas the codelivery of GM-CSF genes resulted in the enhancement of specific antibody response. Kim, et al. further observed that co-delivery of IL-12 gene with a HIV DNA vaccine results in splenomegaly (Kim, et al. 1997, *J. Immunol.*, 158:816–826), which has been shown in mice to have toxic effects such as weight reduction or even death (Eng, et al., 1995, *J. Exp. Med.* 181:1893; Stevensen, et al., 1995, *J. Immunol.* 155:2545; and Orange, et al., 1995, *J. Exp. Med.* 181:901).

Notwithstanding the recent developments in the field of HIV DNA vaccines, there still exists a need for a method to enhance the efficacy of a vaccine, especially an HIV DNA vaccine. For instance, both cellular and humoral immune responses are needed to control an HIV-1 infection (Boyer, et al., 1997, *Nature Medicine* 3:625–532). The induction of both cellular and humoral immune response by the Berjer, et al. method is still quite low because only one of the three immunized chimpanzees developed both cellular and humoral responses. Similarly, although co-delivery of an IL-12 encoding gene with a HIV DNA vaccine, as described in Kim, et al. (1997, *J. Immun.* 158:816–826), may have enhanced the cellular immune response, this co-delivery also decreased the humoral response.

Citation of any of the references discussed hereinabove shall not be construed as an admission that such reference is prior art to the present invention.

4. SUMMARY OF THE INVENTION

The present invention relates generally to the use of chemokines, particularly chemokines which attract lymphocytes or antigen presenting cells, for enhancing an immune response to an antigen, particularly to a vaccine antigen.

In one aspect, the invention relates to a method for enhancing the efficacy of a vaccine in a subject. The method generally comprises administering to the subject: a first component selected from the group consisting of: (i) an antigen against which an immune response is desired in the subject; and (ii) a nucleic acid encoding the antigen of (i). In addition to the first component, the subject is also administered a second component selected from the group consisting of: (i) a chemokine selected from the group consisting of RANTES, MCP-1, MDC and BLC, or a functional equivalent (as defined herein) of said chemokine; and (ii) a nucleic acid encoding the chemokine of (i). The first component and second component are administered in an immunizingly effective amount (as defined herein).

In one aspect of the invention, the second component comprises a human chemokine or a functional equivalent thereof.

In another aspect of the invention, the second component is administered concurrently with the first component. The second component may also be administered within a time period before or after administration of the first component, which time period is sufficient to achieve enhancement of the efficacy of the vaccine.

The first component may be any of a wide variety of antigens known in the art. However, in a preferred embodiment of the invention, the first component is an HIV antigen. A preferred HIV antigen is a gp120 antigen, which in addition to a native gp120, also includes analogs, derivatives and fragments of gp120 which produce an antibody response (i.e., polypeptides which are functionally equivalent in that they produce an antibody response wherein the antibodies produced by such response will bind to native gp120), which antibodies also have specificity for a native HIV gp120.

In another aspect, the invention relates to a nucleic acid encoding both the first component and the second component.

In a method aspect of the invention, the first component and the second component are provided as nucleic acid sequences on the same or on separate nucleic acids and are administered directly to the subject. The first component and the second component may also be provided as nucleic acid sequences on the same or on separate nucleic acids and may be used to transform a cell, which cell is administered to the subject. The first component suitably comprises a nucleic acid encoding an HIV antigen, preferably a gp120 antigen. The subject is preferably a human and may be HIV positive or may exhibit behavioral patterns or occupational factors associated with risk of becoming HIV positive.

In another aspect, the invention relates to a method for improving the speed of an antibody response to a soluble antigen in a subject, comprising co-administering to the subject the soluble antigen with BLC. The soluble antigen is preferably an HIV antigen, more preferably a gp120 antigen. The subject is preferably a human.

The invention also provides a method for reducing the number of immunizations in an immunization regimen required to achieve an improvement in a subject's immune response to an antigen. This method generally comprises administering MDC and the antigen to the subject. The antigen may suitably be administered before, during or after the administration of MDC. However, the antigen is administered in sufficient temporal proximity to the administration of MDC to achieve an improvement in the subject's immune response to the antigen. The antigen is preferably an HIV antigen, and the subject is preferably a human.

In another aspect, the invention provides a method for suppressing an immune response in a subject in need thereof. This method generally comprises administering to the subject an amount of an MCP-1 antagonist which, in comparison to a corresponding immune response in the absence of the MCP-1, suppresses the immune response.

In yet another aspect, the invention provides a method for inducing or enhancing a humoral response in a subject in need thereof, the method comprising administering to the subject a humoral response-inducing amount of BLC.

The invention also relates to a method for inducing a subject to produce MIP-1α. This method aspect of the invention generally comprises administering to the subject an MIP-1α-inducing amount of RANTES. The subject is preferably HIV positive.

The invention also relates to compositions for achieving the various method aspects of the invention. For example, in one aspect, the invention relates to a composition comprising a first component selected from the group consisting of: (i) an antigen against which an immune response is desired in the subject, and (ii) a nucleic acid encoding the antigen of (i); along with a second component selected from the group consisting of: (i) a chemokine selected from the group consisting of RANTES, MCP-1, MDC and BLC, or a functional equivalent of said chemokine, and (ii) a nucleic acid encoding the chemokine of (i). This composition preferably also comprises one or more of each of the following pharmaceutically acceptable components: carriers; excipients; auxiliary substances; adjuvants; wetting agents; emulsifying agents; pH buffering agents; and other components known for use in vaccine or other pharmaceutical compositions.

The invention also relates to a nucleic acid comprising: a first nucleic acid sequence encoding an antigen against which an immune response is desired in the subject; and a second nucleic acid sequence encoding a chemokine selected from the group consisting of RANTES, MCP-1, MDC and BLC, or a functional equivalent of said chemokine. The first and second nucleic acid sequences are preferably expressed in a coordinated manner upon introduction into a subject to produce an amount of the first component that is immunogenic and an amount of the second component that is effective to enhance the efficacy of the vaccine. A related aspect of the invention involves the administration of this nucleic acid to a subject in need thereof to elicit an immune response to the antigen. The nucleic acid is suitably administered as a component of a pharmaceutical composition and may be administered directly to the subject and/or introduced into a suitable host cell and said suitable host cell is administered to the subject. The host cell may be obtained from the subject or from a cell culture originating from one or more cells obtained from the subject.

In a preferred embodiment, the invention provides a method for enhance the efficacy of an HIV vaccine. A preferred polypeptide for use with the HIV vaccine is gp120.

4.1 Abbreviations

| | |
|---|---|
| Ab | antibody |
| APC | antigen presenting cell |
| [m]BLC | [murine] B lymphocyte chemoattractant |
| BCIP/NBT | 5-Bromo-4-chloro-3-indolyl Phosphate/Nitroblue Tetrazolium |
| [m]BLC | [murine] B lymphocyte chemoatttractant |
| BLC | B lymphocyte chemoattractant |
| C | Cysteine |
| C[X]CR | chemokine receptor |
| CTL | cytotoxic T cell |
| ELISA | enzyme linked immunosorbent assay |
| ELISpot | enzyme linked immuno spot |
| FBS | fetal bovine serum |
| HIV | Human Immunodeficiency Virus |
| HIV-1 | human immunodeficiency virus type 1 |
| HIV-1 | human immunodeficiency virus type 1 |
| gp120/140/160 | glycoprotein 120/140/160 |
| HRP | horseradish peroxidase |
| IFN-g | interferon-g |
| IgG | immunoglobulin G |
| Il-2/4 | Interleukin-2/4 |
| MCP-1 | monocyte chemotactic protein-1 |
| [m]MDC | [murine] macrophage-derived chemoattractant |
| MDC | macrophage derived chemokine |
| MIP-1α | macrophage inflammatory protein-1 |
| PBS | phosphate buffered saline |
| PHA | phytohaemagglutinin |
| RANTES | regulated on activation, normally T cell expressed and secreted |
| [m]RANTES | [murine] regulated on activation, normal T cell expressed and secreted |
| Th-type | T helper cell subtype |
| TMB | tetramethylbenzidine |

4.2 Definitions

As used herein, a "pharmaceutically acceptable" component (such as a salt, carrier, excipient or diluent) of a formulation according to the present invention is a component which (1) is compatible with the other ingredients of the formulation in that it can be combined with the active ingredients (e.g. chemokine and/or antigen) of the invention without eliminating the biological activity of the active ingredients; and (2) is suitable for use in animals (including humans) without undue adverse side effects (such as toxicity, irritation, and allergic response). Side effects are "undue" when their risk outweighs the benefit provided by the pharmaceutical composition.

The term "immunizingly effective" is used herein to refer to an immune response which confers immunological cellular memory upon the subject, with the effect that a secondary response (to the same or a similar antigen) is characterized by one or more of the following characteristics: shorter lag phase in comparison to the lag phase resulting from a corresponding exposure in the absence of immunization; production of antibody which continues for a longer period than production of antibody for a corresponding exposure in the absence of such immunization; a change in the type and quality of antibody produced in comparison to the type and quality of antibody produced from such an exposure in the absence of immunization; a shift in class response, with IgG antibodies appearing in higher concentrations and with greater persistence than IgM; an increased average affinity (binding constant) of the antibodies for the antigen in comparison with the average affinity of antibodies for the antigen from such an exposure in the absence of immunization; and/or other characteristics known in the art to characterize a secondary immune response.

The term "functional equivalent" with respect to a polypeptide (e.g., a chemokine or antigen) as used herein refers to a polypeptide sequence comprising the full length amino acid sequence of the polypeptide, or comprising a fragment, analogue, derivative or truncation isoform of the polypeptide. Functional equivalents also include, for example, the polypeptide, or its fragment, analogue, derivative or truncation isoform, in salt, complex, or analog form. Functional equivalents retain some or all of the biological activity of the corresponding polypeptide. Where the polypeptide referred to is an antigen, "biological activity" refers to the ability of the functional equivalent to bind to an antibody that will also bind to the native antigen.

The terms "peptide," "polypeptide," and "protein" are used interchangeably herein and are intended to refer to amino acid sequences of any length.

5. BRIEF DESCRIPTION OF THE FIGURES

FIGS. 1A and 1B. The nucleotide and amino acid sequences of MDC. 1A depicts the nucleotide sequence of MDC (SEQ ID NO: 1), with the coding region indicated by the appearance of the amino acid sequence in the line below; and 1B depicts the amino acid of MDC (SEQ ID NO:2) from GenBank accession no. U83171 (Godiska, et al., 1997, *J. Exp. Med.* 185:1595–1604).

FIG. 2A. DNA immunization regimen with either pcDNABaLgp120 or pcDNABaLgp160 and one of the chemokine constructs, pcBLC, pcMCP-1, pcMDC or pcRANTES. Injections were performed three times and were separated by two weeks each. At three weeks post-final injection, blood samples were taken again, and at 9 weeks post-final injection, mice were sacrificed, splenocytes pooled and used for Th cell proliferation, ELISpot and Th-associated cytokine expression assays.

Figure 2B:
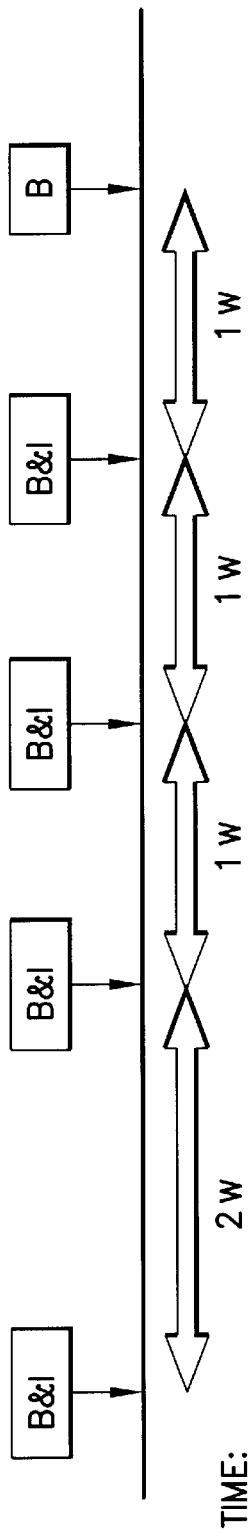

FIG. 2B. Protein immunization regimen for separated injection of MDC and ovalbumin (1 couple with 18 hours separation) into the base of the tail. Four injection couples were performed weekly, apart from the second, which was performed two weeks after the first one.

Figure 3A:
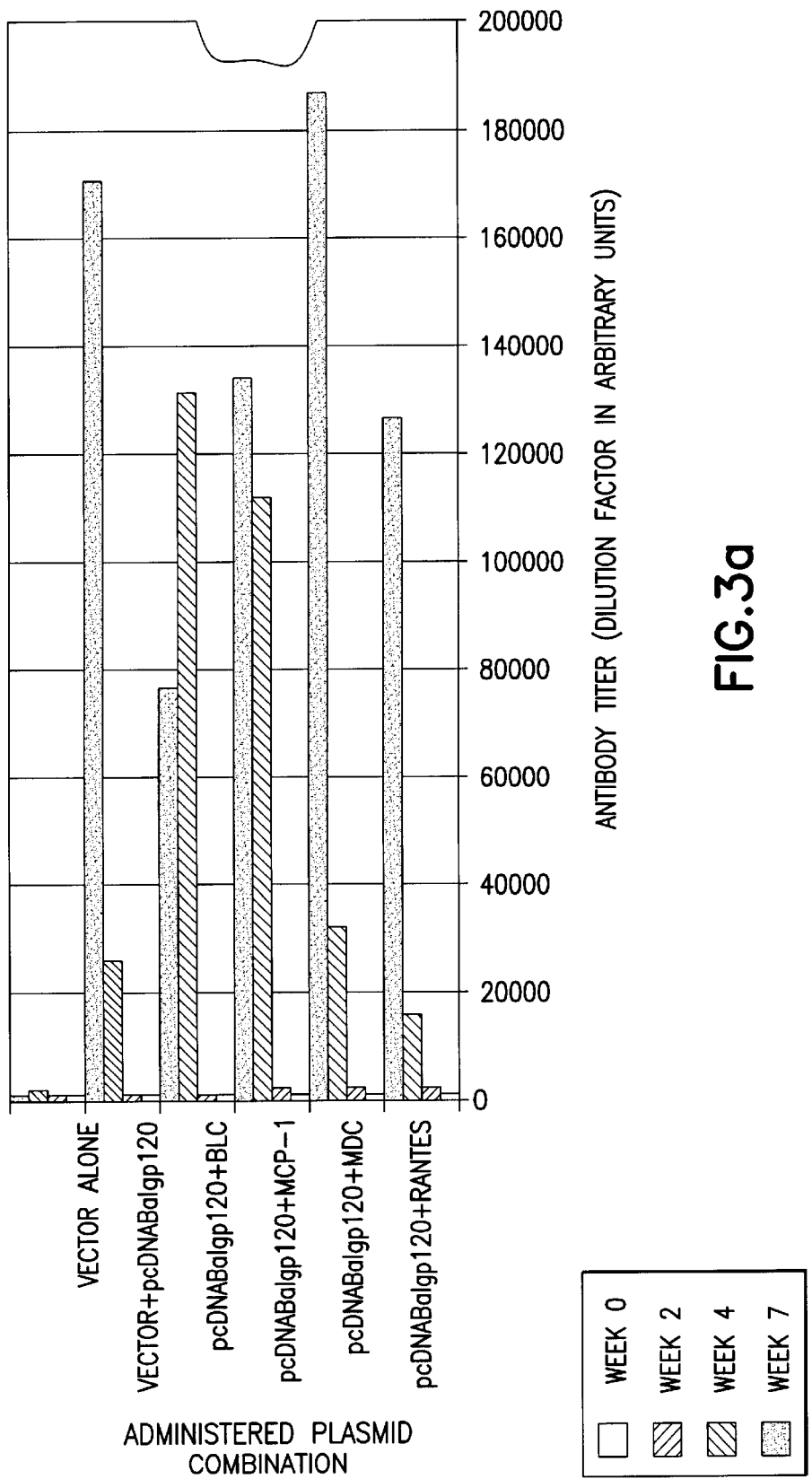

FIG. 3A. Antibody titer after vaccination with pcDNA-Balgp120 and different plasmid derived chemokines. The injections were performed 1.m. into the tibialis anterior, 11 days following an injection of cardiotoxin, at weeks 0, 2 and 4 and under anaesthesia with 1 µl of ketamine-xylazine mix per gram mouse. Blood samples in order to detect the antibody liter against rgp140were taken at the morning of each day of injection, the serum was collected after separating the cellular plate with anti-gp120 and capturing with rgp140 over an average of 4 animals per group. The total amount of administered DNA per injection was 100 µg per leg, equally distributed between the plasmid encoded antigen pcDNABalgp120and the coadministered chemokine encoding plasmids. The titer of the first two bleeds at week 0 are too low to appear in the graph. The transparent bars represent the titer at week 7.

Figure 3B:
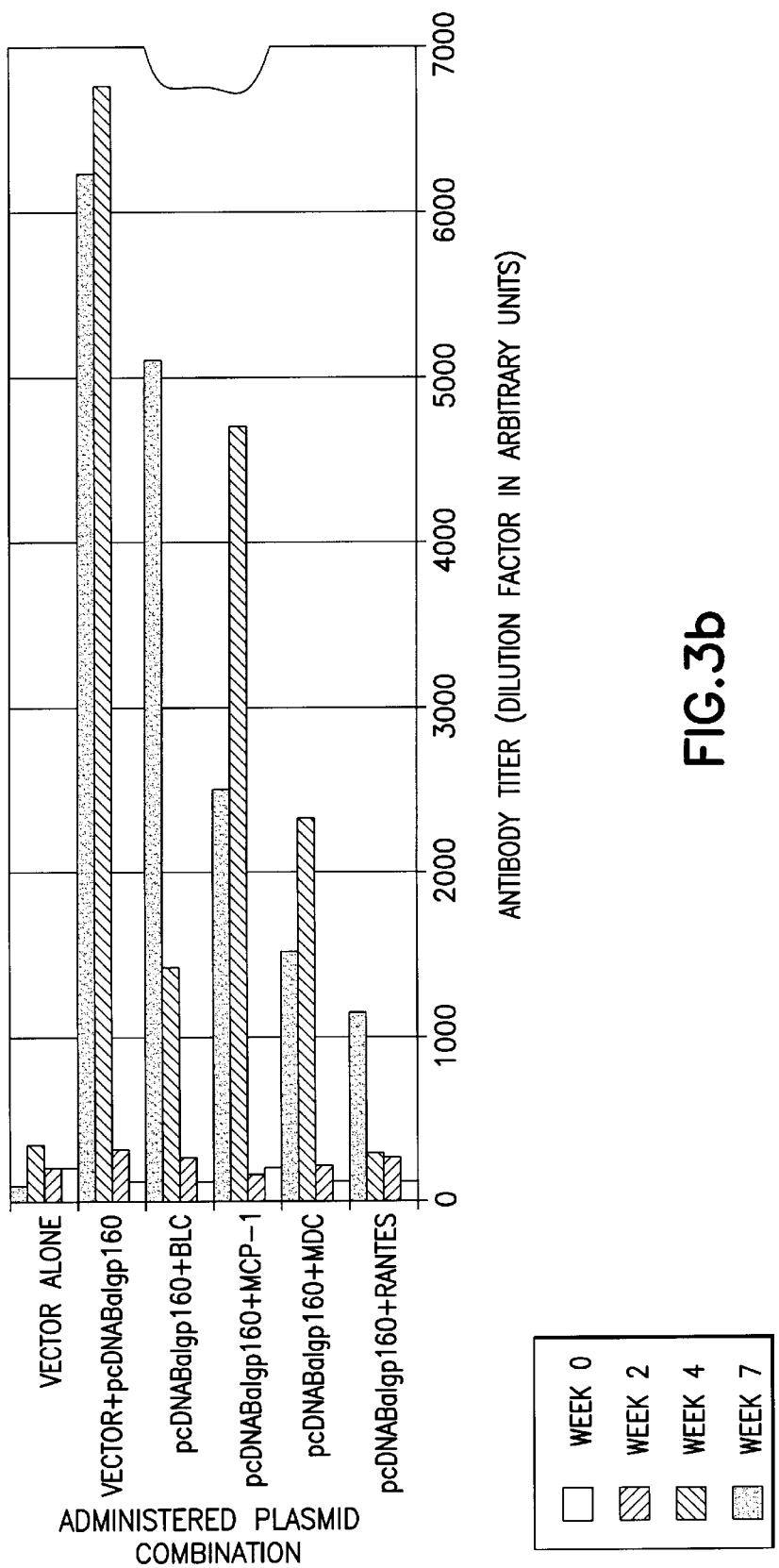

FIG. 3B. Antibody titer after vaccination with pcDNAB-galp180 and different plasmid derived chemokines. The injections were performed 1.m. into the tibialis anterior, 11 days following an injection of cardiotoxin, at weeks 0, 2 and 4 and under anaesthesia with 1 ul of ketamine-xylazine mix per gram mouse. Blood samples in order to detect the antibody titer against rgp140were taken at the morning of each day of injection, the serum was collected fraction by centrifuging at 5000 rpm for 5 minutes. The titer was obtained by means of a capture ELISA after coating the plate with anti-gp120 and capturing with rgp140 over an averge of 4 animals per group. The total amount of administered DNA per injection was 100 ug per leg, equally distributed between the plasmid encoded antigen pcDNABalgp160 and the coadministered chemokine encoding plasmids. The transparant bars represent the titer at week 7. Abbreviations: BLC B lymphocyte chemokine; MCP-1, monocyte chemoattractant protein-1; MDC, macrophage derived chemokine; RANTES: regulated upon activation, normal T cell expressed and secreted.

FIG. 4. Total IgG-antil ovalbumine titer, of protein vaccination assay with mMDC as adjuvant in Balb/c mice (n=4). Injections were performed in the base of the tail in a volume of 15 ul sterile saline for both, the antigen and the chemokine. One injection couple is composed of an injection of mMDC in concentrations ranging from 0 µg (negative control) to 3 µg and an injection of 10 ug chicken ovalbumine at a time point 18 h post chemokine injection. Blood samples were taken retroorbitally at the morning of the day of the mMDC injection and the serum fraction stored frozen. The negative control was injected with PBS only, the positive control with 15 ul incomplete Freund's adjuvant.

Figure 5A:
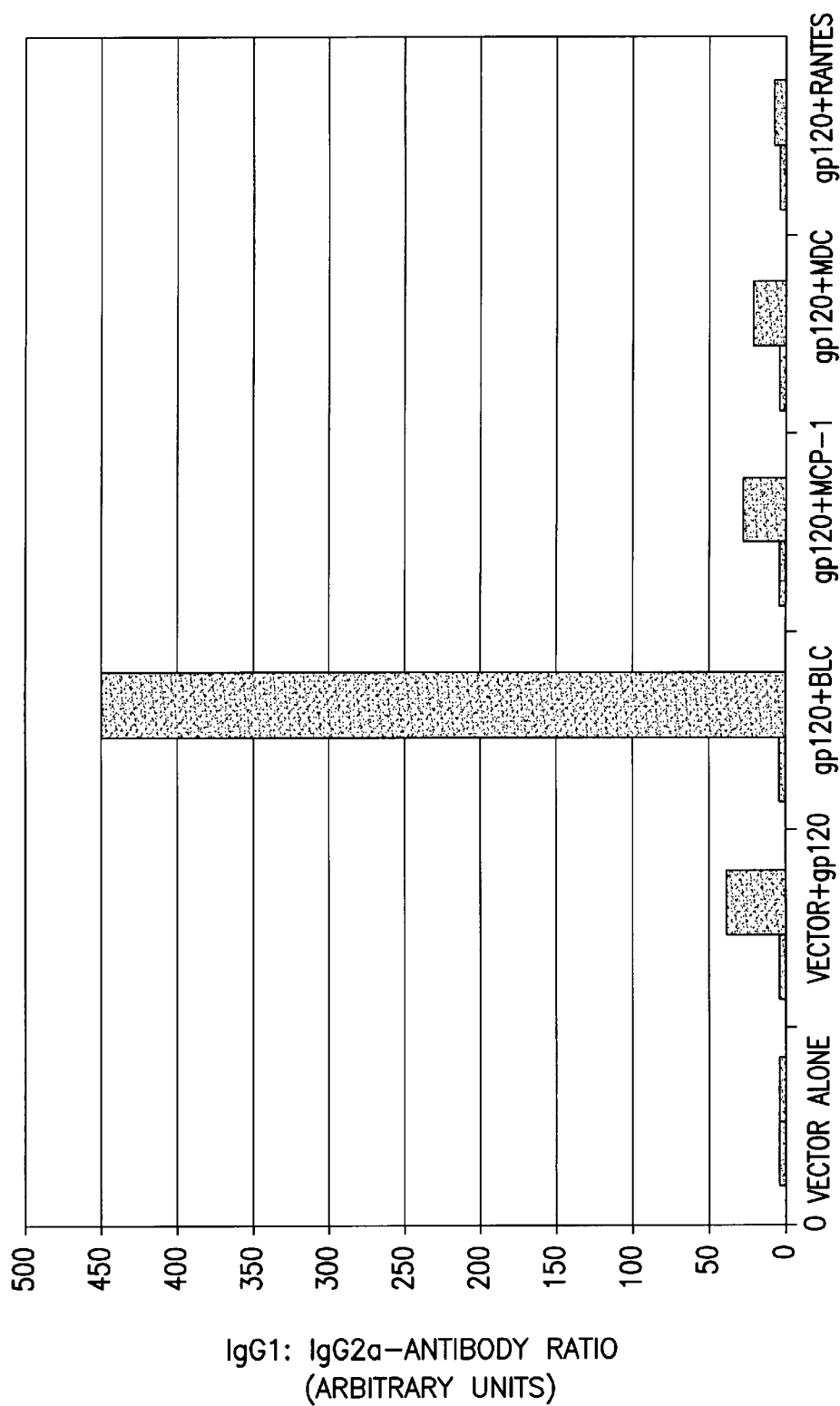

FIG. 5A. Shift in IgG1:IgG2a ration after gp120 vaccination in presence of chemokines (rgp140 capture ELISA). The situation prior and upon the immunization regimen is compared. IgG1:IgG2a ratios are represented as bars in the figure and are proportional to the Th2-like immunoresponse.

Figure 5B:
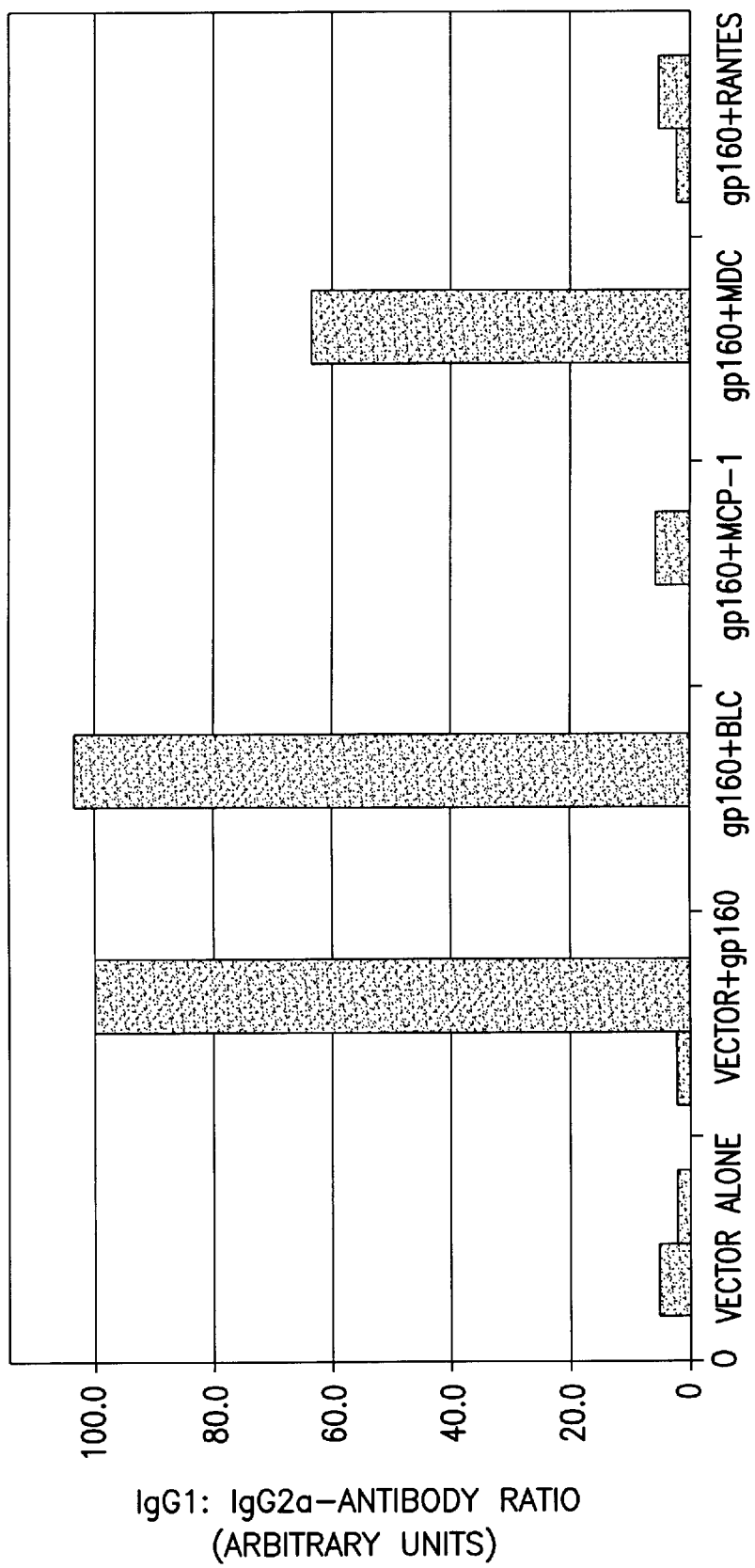

FIG. 5B. Shift in IgG1:IgG2a retio after gp160 vaccination in presence of chemokines (rpg140 capture ELISA). The situation prior and upon the immunization regimen is compared. IgG1:IgG2a ratios are represented as bars in the figure and are proportional to the Th2-like immunoresponse.

Figure 6:
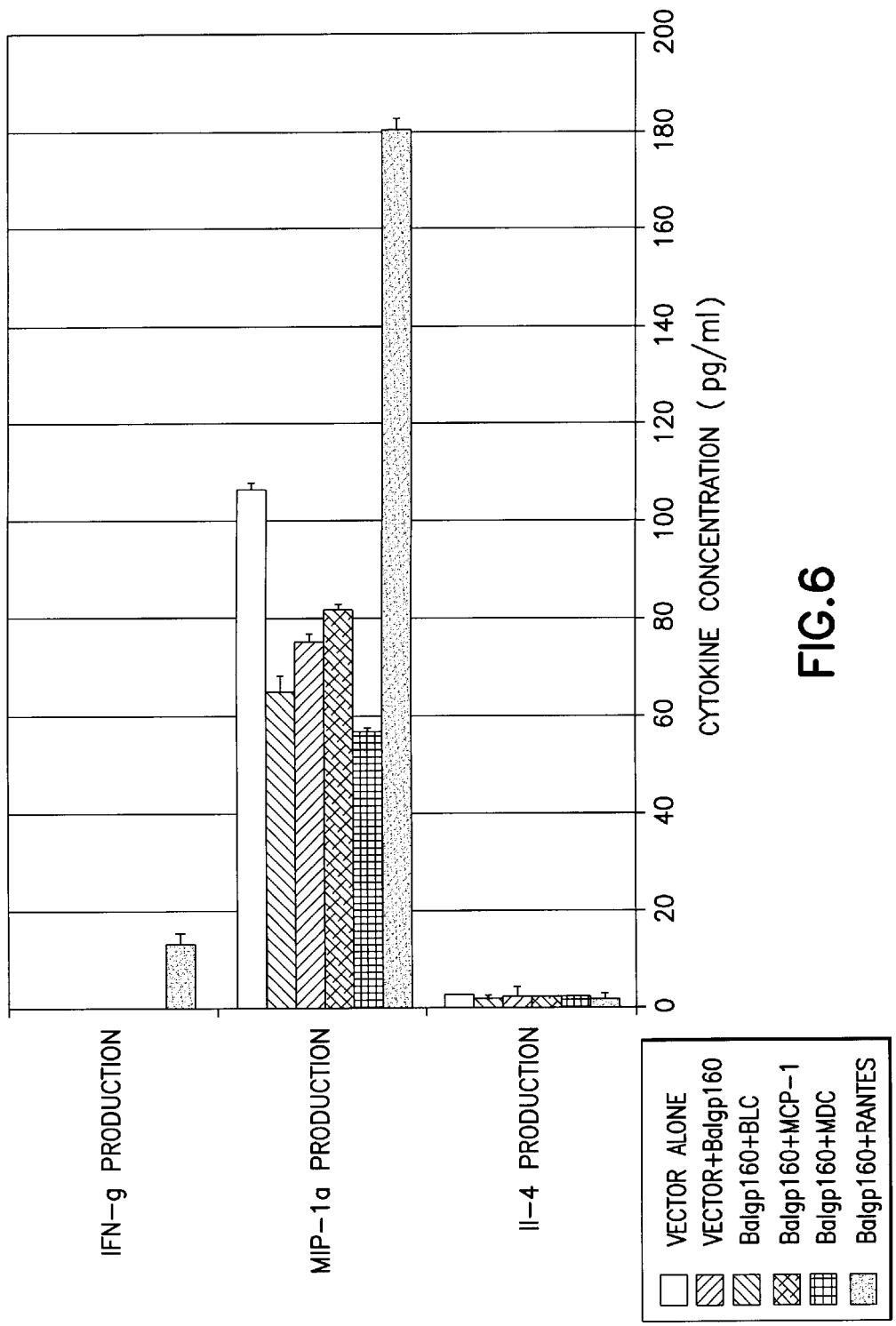

FIG. 6. The type related cytokine production in splenocyte culture supernatants of chemokine and pCDNA-Balgp160 co-immunized mice. Prior to splenocyte culturing, the mice were immunized 3 times into the muscle tibialis anterior with 100 ug DNA, equally distributed between antigen expression plasmid and chemokine expression plasmid. The splenocytes, after separation from the erythrocytes, were kept in culture in complete RPM with 10% FBS for three days. The supernatants were diluted in RPM (10% FBS) 1:30.7 in the case of IFN-γ or 1:3.07 I the case of MIP-1a and IL-4, respectively and the resulting data is represented in pg/ml. The injected plasmid combinations are represented in the legend. The values represented for IFN-g and IL-4 had to be extrapolated, their confidence is low.

Figure 7:
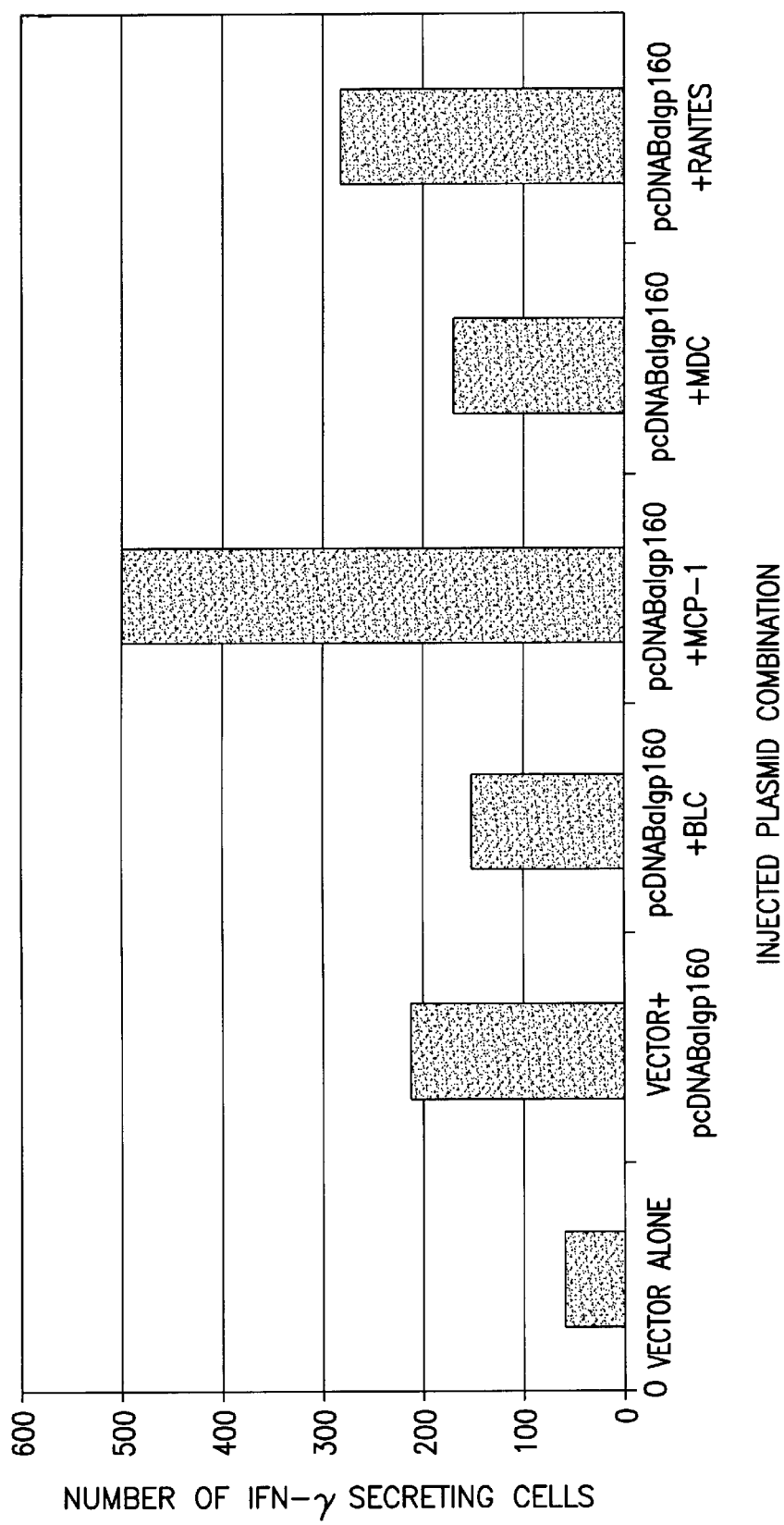

FIG. 7. Number of IFN-γ secreting cells as determined by ELISPOT assay. After injecting groups of 4 mice 3 times with 100 µg DNA per leg in different combinations of chemokines and pcDNABaLgp160 (see X-axis) at weeks 0, 2 and 4, splenocytes were recovered at week suspensions were diluted and 1 million were cultured in the presence of the same number of irradiated P815 stimulator cells for 6 days. Then, 0.1 million effector-splenocytes were challenged with V3-pulsed P85 stimulator cells at a ratio 3:1 in 270 ul RPMI in anti-IFN-γ coated Millipore HA ELISPOT plates over night at 37° C. The following day, the number of IFN-γ secreting cells was counted after washing out the cells, incubating with streptavidine conjugated anti-IFN-γ Abs for 2 h, incubating with the substrate for 2 h and waiting for the major spots to be developed (5 minutes).

6. DETAILED DESCRIPTION OF THE INVENTION

The present invention relates to a method for enhancing the efficacy of a vaccine in a subject comprising administering to the subject (i) an antigen or a nucleic acid encoding an antigen and (ii) a chemokine and/or functional equivalent thereof or a nucleic acid encoding a chemokine and/or functional equivalent of the chemokine.

In empirical work supporting the present application, the following four chemokines were compared:

RANTES (regulated on activation, norrnally T cell expressed and secreted), which has a broad chemoattractant activity, for T cells and monocytes/macrophages, as well as basophils, eosinophils, natural killer cells, mast cells and dendritic cells, but is unable to attract B cells. It functions through CCR-1. CCR-3, CCR-5 and CCR-9 (Kim, C. H. et al., 1999).

MCP-1 (monocyte chemotactic protein-1), which is chemoattractant for monocytes and T cells, as well as monocytes/macrophages, basophils, eosinophils, natural killer cells, mast cells and hematopoietic progenitor cells (Yoshimura, T., 1989) via the receptors CCR2B and CCR-9 (Kim, C. H., et al., 1999).

MDC (macrophage-derived chemoattractant), which causes chemotaxis of monocytes/macrophages, activated natural killer cells and dendritic cells (Bochner, B. S., et al., 1999) by activating via CCR4 (Bochner, B. S., et al., 1999), although there are indications that MDC also functions via other still unknown receptors (Bochner, B. S., 1999; Struyf, S., 1998).

BLC (B lymphocyte chemoattractant) is involved mostly in chemotaxis of B lymphocytes (Legler, D. F., et al., 1998). It induces the formation of germinal centers by directing B cells to follicles of secondary lymphoid tissues (Foerster, R., 1996) and functions via CXCR5 (BLR-1 or BCA-1) (Gunn, M. D., et al., 1998).

The receptor-specificity, cellular expression patterns and their chemoattractant are set forth in the following table:

TABLE 1

Chemokines used for immunizations, their classes, receptors, sources and target cells.
Abbreviations: I) the chemokines: BLC/BCA-1, B-cell attracting chemokine; MCP-1, monocyte chemoattractant protein-1; MDC, macrophage derived chemokine; RANTES: regulated upon activation, normal T cell expressed and secreted;
II) the sources/target cells: B, B lymphocytes; Ba, Basophils; DC, Dentritic Cells; E, Eosinophils, F, Fibroblasts; HPC, Hemotopoietic Progenitor Cells, M, Monocytes/Macrophages; MC, Mast Cells; ME, Mesangial Cells; N, Neutrophils; T, T lymphocytes.

| Chemokine | Class | Receptor | Source | Target Cells |
|---|---|---|---|---|
| BLC/BCA-1 | CXC (α) | CXCR5 | Liver, Spleen, lymph node | B |
| MCP-1 | CC (β) | CCR2 | F, M, L, EC, EP, tumor cell lines | M, T, E, Ba, NK, HPC, MC |
| MDC | CC (β) | CCR4 (more?) | DC, M, T | DC, M, NK |
| RANTES | CC (β) | CCR1, CCR3, CCR5 | F, M, T, ME, various cell lines | M, T, Ba, E, NK, MC, DC |

For clarity of disclosure, and not by way of limitation, the detailed description of the invention is divided into the subsections which follow.

6.1 Chemokines as Modulators of Immune Response

We hypothesized that RANTES, MCP-1, MDC, and BLC could modulate the elicitation of antigen-specific immune response. Such modulation would depend on the cell types responsive to each chemokine. Accordingly, we investigated these chemokines in immunization experiments using HIV-$1_{Bal}$ Gp 120 and gp 160 as antigens. Modulation of immune response has been shown for several chemokines and cytokines, such as 11–12 (Sin, J. L. et al., 1999), 11-2, 11-4 and 11-10 (Chun, S., et al.,1998), RANTES (Xin, K. Q., et al., 1999), and MCP-1 (Ki,m J. J., et al., 1998). However, there is a critical lack of data investigating the role of chemokines in modulating immune response in a comparative way, and chemokines that are potentially important in recruiting antigen presenting cells (APCs) have not been investigated.

Possible mechanisms for modulation of the immune response by chemokines might involve augmented probability of assembling a target (antigen or antigen presenting cell (APC)) and effector (B or T cell) by chemoattraction. In addition, chemokine-mediated direct activation of the cells involved in the immune response may also take place in this system: locally increased chemokine concentration can stimulate the attracted cells in a paracrine manner (Behringer, D., 1997). Finally, the interaction between effector cells and APCs, upon recruitment by chemokines, namely CD4-T cells (helper cells) and CDδ T cells or B cells, leads to mutual activation. In fact, the encounter of the antigen by its specific effector cells induces proliferation and/or differentiation.

In order to evaluate modulation of the immune response, we measured production of antigen specific antibodies (Abs) as an indicator of humoral immunity and the antigen-specific induction of interferon-γ-producing (IFN-γ) cells as marker for specific cytotoxic T lymphocytes (CTLS) in mixed lymphocyte assays. In addition, we evaluated the T helper (Th) cell profile, following the expression of the antigen and the reaction of the attracted cells in presence of the different chemokines, using different markers. The ratio of the immunoglobulin isotypes IgG1 and IgG2a and the production of the cytokines (Street, N. E. and Mosmann, T. R., 1991) in non-stimulated effector cell cultures: Interleukin-4 (IL-4), which is Th2-type associated, INF-γ, which is Th1-type associated) and further macrophage inflammatory protein-1α (MIP-1α).

In the case of MDC we also explored the immunomodulatory activities of this chemokine in a protein vaccination protocol, evaluating the dose dependency of the induced immune reaction. The results demonstrate the usefulness of tailoring immunization protocols by adding one or more chemokines at specific amounts to elicit an immune response of a desired profile regarded as most adequate to fight a pathogen or a neoplastic cell.

6.2 Methods and Compositions for Enhancing the Efficacy of a Vaccine

Where nucleic acids encoding the antigens and/or chemokines are employed, it will be understood that the respective coding sequences are operatively linked to gene regulatory sequences capable of directing the expression of the sequences upon administration to a subject and/or introduction into a suitable cell. For example, such coding sequences will preferably be expressable in a cell of a subject, preferably in a cell of a human subject.

The present invention provides methods for enhancing the efficacy of a vaccine in a subject, which methods comprise administering to a subject an immunizingly effective amount of one or more antigens against which an immune response is desired in the subject in conjunction with an amount of a chemokine or its functional equivalent effective to enhance the immune response against the antigen. In one aspect, the chemokine or its functional equivalent, is administered to the subject concurrently with (e.g., in the same composition with) the antigen or antigens against which an immune response is desired. In another, aspect, the chemokine or its functional equivalent, is administered either before or after the administration of one or more antigens against which immunity is desired in the subject, but is administered within such time that the chemokine or its functional equivalent enhances the immune response to the one or more antigens. For example, the chemokine or its functional equivalent is suitably administered during the time that the subject mounts an immune response against the administered one or more antigens. The chemokine or its functional equivalent is preferably administered within 30 minutes, 1 hour, 5 hours, 10 hours, 1 day, and/or 2 days of (preferably, after) administration of the one or more antigens against which immunity is desired. In a preferred embodiment, the site of administration of the chemokine is at or near the site of administration of the antigen.

The present invention further provides compositions comprising an immunizingly effective amount of one or more antigens and an amount of chemokine or its functional equivalent, effective to enhance the immune response to said antigen and, preferably, the composition further comprises a pharmaceutically acceptable carrier.

Any chemokine that is capable of enhancing the efficacy of a vaccine (for example, but not limited to, as determined by the assays described in Section 5.4, infra) can be used in the methods and compositions of the present invention.

In one specific embodiment the chemokine component is full length MDC, preferably full length MDC having the amino acid sequence of SEQ ID NO:2 (FIG. 1B). In another embodiment, the chemokine component consists of amino acid residues 2–69 of SEQ ID NO:2 (FIG. 1B). In another specific embodiment chemokine component consists of amino acid residues 3–69 of SEQ ID NO:2 (FIG. 1B). In still another specific embodiment the N-terminal amino acid sequence of the chemokine component consists of the amino acid sequence Tyr-Gly-Ala-Asn-Met-Glu-Asp-Ser-Val-Cys-Cys-Arg-Asp-Tyr-Val-Arg-Tyr-Arg-Leu (portion of SEQ ID NO:2). In yet another specific embodiment the N-terminal amino acid sequence of the chemokine protein consists of the amino acid sequence Pro-Tyr-Gly-Ala-Asn-Met-Glu-Asp-Ser-Val-Cys-Cys-Arg (portion of SEQ ID NO:2). In yet another specific embodiment the N-terminal amino acid sequence of the chemokine consists of the amino acid sequence Tyr-Gly-Ala-Asn-Met-Glu-Asp-Ser-Val-Cys-Cys-Arg-Asp-Tyr-Val-Arg-Tyr-Arg-Leu (SEQ ID NO:2), which derivative has activity to enhance the efficacy of the vaccine. In yet another specific embodiment the N-terminal amino acid sequence of the chemokine consists of the amino acid sequence Pro-Tyr-Gly-Ala-Asn-Met-Glu-Asp-Ser-Val-Cys-Cys-Arg (SEQ ID NO:2), which derivative has activity to enhance the efficacy of the vaccine.

In yet another specific embodiment, the chemokine component is a derivative of a corresponding native chemokine, which derivative has one or more insertions of or substitutions with one or more non-classical amino acids relative to the native chemokine, which derivative will enhance the efficacy of the vaccine.

In yet another specific embodiment, the chemokine is a derivative of a corresponding native chemokine that has only one or more conservative substitutions in sequence relative to the native chemokine, which derivative enhances the efficacy of the vaccine.

Chemokines useful in the present invention may be derived from any suitable source and obtained by any method known in the art.

Preferably, the chemokine is of the same species as the subject to which the vaccine is administered. In a preferred embodiment, a human chemokine is administered to a human subject.

The present invention also provides a method to enhance the efficacy of a vaccine in a subject, which method comprises administering to a subject a first nucleic acid comprising a nucleotide sequence encoding an antigen against which an immune response is desired in a subject and a second nucleic acid comprising a nucleotide sequence encoding chemokine and/or its functional equivalent. The expression of the encoded antigen and the chemokine or its functional equivalent, is suitably controlled of one or more gene regulatory elements. Such regulatory elements are known in the art, and examples are described herein. Regulatory elements are selected and arranged so that upon introduction of the first and second nucleic acids into a suitable cell (e.g., a cell of the subject), the antigen and chemokine or its functional equivalent are coordinately expressed. Coordinate expression occurs where (i) the two components are expressed either at the same time or within an appropriate time period, i.e., the time period is sufficient for the chemokine to enhance the immune response against the antigen). Moreover, the antigen is preferably expressed in an immunizingly effective amount; and (iii) the chemokine or its functional equivalent is expressed in an amount sufficient to enhance the immune response against the antigen.

In a specific embodiment, the nucleotide sequences encoding (i) the chemokine or its functional equivalent and (ii) the antigen are present on separate nucleic acids. In another embodiment, the nucleotide sequences encoding (i) the chemokine or its functional equivalent and (ii) the antigen are present on the same nucleic acid.

The present invention also provides compositions to enhance the efficacy of a vaccine in a subject. The compositions generally comprise a first nucleic acid comprising a nucleotide sequence encoding an antigen and a second nucleic acid comprising a nucleotide sequence encoding a chemokine, wherein the nucleotide sequences encoding the antigen and the chemokine are operably linked to one or more gene regulatory elements such that, upon introduction of said first and second nucleic acids (or a single nucleic acid comprising both) into a suitable cell (e.g., a cell of the subject), the antigen and chemokine are expressed, preferably in a coordinated manner. The antigen and the chemokine are expressed in a manner which results in an immunizingly effective response.

The present invention also provides compositions to enhance the efficacy of a vaccine in a subject. These compositions generally comprise a nucleic acid comprising a first nucleotide sequence encoding an antigen and a second nucleotide sequence encoding a chemokine or its functional equivalent. The first and second nucleotide sequences may be joined to form a single nucleotide sequence encoding both the antigen component and the chemokine component. The first and second nucleotide sequences are each operably linked to one or more gene regulatory elements such that, upon introduction into a suitable cell, the antigen and the chemokine are expressed, preferably in a coordinated manner. The antigen and the chemokine are expressed in a manner which results in an immunizingly effective response.

Any nucleic acid comprising a nucleotide sequence encoding an chemokine or its functional equivalent capable of enhancing the immune response to the antigen can be used in the methods and compositions of the present invention.

Preferred chemokine components are RANTES, MDC, MCP-1 and BLC, and functional equivalents of these chemokines.

In another specific embodiment, the method or composition of the invention uses a nucleic acid encoding a chemokine derivative having one or more deletional, insertional or substitutional mutations, which derivative has activity to enhance an immune response against an antigen in a subject.

DNA vaccines according to the invention are suitably produced by any method known in the art for constructing an expression plasmid vector encoding for expression the nucleotide sequences of (i) an antigen; and/or (ii) a chemokine. Regulatory elements are selected to provide a vector suitable for expression of the encoded proteins in the subject or in cells recombinant for the expression vector, which cells are to be provided to the subject. Such expression vectors typically comprise promoters, terminators and polyadenylation coding regions to control the expression of the encoded protein.

The DNA vaccine can be administered by any method known in the art for administration of DNA. The DNA vaccine may be delivered either directly, in which case the subject is directly exposed to the DNA vaccine such that the DNA enters and is expressed in cells of the subject, or indirectly, in which case, the DNA vaccine is first introduced into suitable cells by any method known in the art in vitro, then the cells containing the DNA vaccine are transplanted into the subject.

In a specific embodiment, the DNA vaccine is directly administered in vivo, where it is expressed to produce the encoded antigen and chemokine. This can be accomplished by any of numerous methods known in the art. The chemokine-encoding nucleic acid and the antigen-encoding nucleic acid can be provided as components of one or more nucleic acid expression vector (i.e., the chemokine-encoding nucleic acid and the antigen-encoding nucleic acid can be components of the same or separate expression vectors) and administering the vector (or vectors) so that it becomes intracellular. Methods for administration of vectors are known in the art. Examples include infection using a defective or attenuated retroviral or other viral vector (see U.S. Pat. No. 4,980,286); direct injection of naked DNA; microparticle bombardment (e.g., a gene gun; Biolistic, Dupont); coating with lipids or cell-surface receptors or transfecting agents; encapsulating the vector in liposomes, microparticles, or microcapsules; administering the vector linked to a peptide which is known to enter the nucleus; administering the peptide linked to a ligand subject to receptor-mediated endocytosis (see e.g., Wu and Wu, *J. Biol. Chem.* 262:4429–4432 (1987)) (which can be used to target cell types specifically expressing the receptors). In another embodiment, a nucleic acid-ligand complex can be formed in which the ligand comprises a fusogenic viral peptide to disrupt endosomes, allowing the nucleic acid to avoid lysosomal degradation. In a preferred embodiment, the nucleic acid of a DNA vaccine is injected into the muscle of the subject to be immunized.

Another approach is to introduce the nucleic acid of the DNA vaccine into a cell prior to in vivo administration of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign nucleic acid into cells (see e.g., Loeffler and Behr, *Meth. Enzymol.* 217:599–618 (1993); Cohen, et al., *Meth. Enzymol.* 217:618–644 (1993); Cline, *Pharmac. Ther.* 29:69–92 (1985)) and may be used in accordance with the present invention. Usually, the method of transfer includes the transfer of a selectable marker to the cells. Known techniques are then used to isolate those cells that have taken up and are expressing the transferred gene.

Cells into which a DNA vaccine can be introduced for purposes of immunization encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

The resulting recombinant cells can be delivered to a subject by various methods known in the art. In a preferred embodiment, the recombinant cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The cells can also be encapsulated in a suitable vehicle and then implanted in the subject (see, e.g., Dionne, et al. PCT Publication WO 92/19195, dated Nov. 12, 1992). The amount of cells envisioned for use depends on the desired effect, subject state, etc., and can be determined by one skilled in the art without undue experimentation.

By way of example, and not by way of limitation, a DNA vaccine may be generated as described by Lekutis, et al. for an HIV DNA vaccine (1997, *J. Immunol.* 158:4471–4477). Briefly, an expression vector is constructed with the promoter, enhancer and intron A of human cytomegalovirus (CMV) and the termination and polyadenylation sequences of bovine growth hormone in a plasmid backbone. Additionally, the nucleotide sequence for signal sequence of tissue plasminogen activator is either substituted for the signal sequence of the antigen, if the antigen has a signal sequence or is added onto the amino-terminus of the antigen, thereby eliminating the dependence on viral proteins for expression (e.g., in the case of gp120 expression, Rev and Env proteins are required unless the HIV-1 signal sequence is so substituted). The resulting formulation is then injected intramuscularly.

Further examples of DNA vaccines are set forth in Boyer, et al. (1996, *J. Med. Primatol.,* 25:242–250), which describes the construction of a plasmid encoding the HIV-1 gp160 envelope glycoprotein as well as the rev-tax region cloned into pMAMneoBlue vector (Clonetech, Inc., Palo Alto, Calif.), and a vector encoding the envelope glycoprotein and Rev from HIV-1 strain MN under the control of the CMV promoter. Another vector which can be used in the present invention is as described in Boyer, et al. (1997, *Nature Medicine* 3:526–532) and contains expression cassettes encoding the envelope and Rev proteins of HIV-1 strain MN, and encoding the Gag/Pol proteins of HIV-1 strain IIIB.

For the practice of the present invention, the nucleotide sequence for the chemokine or its functional equivalent, can either be incorporated into the same expression vector containing the nucleotide sequence encoding the antigen in such a manner that the chemokine is expressed. Alternatively, the nucleotide sequence encoding chemokine, or a functional equivalent thereof, can be cloned into a separate expression vector (e.g., as described above for the expression vector containing the sequences coding for antigen) and the expression vector that expresses the antigen mixed with the expression vector that expresses chemokine. The mixture of the two expression vectors can then be administered to the subject.

The methods and compositions of the present invention may be used as a vaccine in a subject in which immunity for the antigen(s) is desired. Such antigens can be any antigen known in the art to be useful in a vaccine formulation. The methods and compositions of the present invention can be used to enhance the efficacy of any vaccine known in the art. The vaccine of the present invention may be used to enhance an immune response to infectious agents and diseased or abnormal cells, such as but not limited to bacteria, parasites, fungi, viruses, tumors and cancers. The compositions of the invention may be used to either treat or prevent a disease or disorder amenable to treatment or prevention by generating an immune response to the antigen provided in the composition. In one preferred embodiment, the antigen(s) are proteins or fragments or derivatives thereof encoded by any genes of the HIV genome including the env, gag, pol, nef, vif, rev, and tat genes. In a more preferred embodiment, the antigen is an HIV associated gp120 protein.

The methods and compositions of the present invention may be used to elicit a humoral and/or a cell-mediated response against the antigen(s) of the vaccine in a subject. In one specific embodiment, the methods and compositions elicit a humoral response against the administered antigen in a subject. In another specific embodiment, the methods and compositions elicit a cell-mediated response against the administered antigen in a subject. In a preferred embodiment, the methods and compositions elicit both a humoral and a cell-mediated response.

The subjects to which the present invention is applicable may be any mammalian or vertebrate species, which include, but are not limited to, cows, horses, sheep, pigs, fowl (e.g., chickens), goats, cats, dogs, hamsters, mice and ratsmice, monkeys, rabbits, chimpanzees, and humans. In a preferred embodiment, the subject is a human. The compositions and methods of the invention can be used to either prevent a disease or disorder, or to treat a particular disease or disorder, where an immune response against a particular antigen or antigens is effective to treat or prevent the disease or disorder. Such diseases and disorders include, but are not limited to, viral infections, such as HIV, CMV, hepatitis, herpes virus, measles, etc., bacterial infections, fungal and parasitic infections, cancers, and any other disease or disorder amenable to treatment or prevention by eliciting an immune response against a particular antigen or antigens. In another preferred embodiment, the subject is infected or at risk of being infected with HIV virus.

In another preferred embodiment, the invention provides methods and compositions to enhance the efficacy of an HIV vaccine, and such a vaccine can be administered to either prevent or treat HIV.

6.3 Chemokine Nucleic and Amino Acid Sequence and Functional Equivalents

The chemokine amino acid and nucleic acid sequences used in the methods and compositions of the invention can be obtained by any method known in the art. Chemokine nucleotide and amino acid sequences for humans and other animals are publically available in public databases. For examples the Genbank Accession Nos. for MDC; MCP-1; RANTES; and BLC are set forth in the following table (as obtained from http://www2.ncbi.nlm.nih.gov/genbank/query_form.html):

| CHEMOKINE | GENBANK ACCESSION NO. | SEQUENCE | | | | |
|---|---|---|---|---|---|---|
| Homo sapiens macrophage derived chemokine (MDC) | U83171 | 1 gagacataca | ggacagagca | tggctcgcct | acagactgca | ctcctggttg tcctcgtcct |
| | | 61 ccttgctgtg | gcgcttcaag | caactgaggc | aggccccctac | ggcgccaaca tggaagacag |
| | | 121 cgtctgctgc | cgtgattacg | tccgttaccg | tctgcccctg | cgcgtggtga aacacttcta |
| | | 181 ctggacctca | gactcctgcc | cgaggcctgg | cgtggtgttg | ctaaccttca gggataagga |
| | | 241 gatctgtgcc | gatcccagag | tgccctgggt | gaagatgatt | ctcaataagc tgagccaatg |
| | | 301 aagagcctac | tctgatgacc | gtgtgccttgg | ctcctccagg | aaggctcagg agccctacct |
| | | 361 ccctgccatt | atagctgctc | cccgccagaa | gcctgtgcca | actctctgca ttccctgatc |
| | | 421 tccatccctg | tggctgtcac | ccttggtcac | ctccgtgctg | tcactgccat ctcccccctg |
| | | 481 accctctaa | cccatcctct | gcctccctcc | ctgcagtcag | agggtcctgt tcccatcagc |
| | | 541 gattcccctg | cttaaaccct | tccatgactc | cccactgccc | taagctgagg tcagtctccc |
| | | 601 aagcctggca | tgtgccctc | tggatctggg | ttccatctct | gtctccagcc tgcccacttc |
| | | 661 ccttcatgaa | tgttgggttc | tagctccctg | ttctccaaac | ccatactaca catcccactt |
| | | 721 ctgggtcttt | gcctgggatg | ttgctgacac | tcagaaagtc | ccaccacctg cacatgtgta |
| | | 781 gccccaccag | ccctccaagg | cattgctcgc | ccaagcagct | ggtaattcca tttcatgtat |
| | | 841 tagatgtccc | ctggccctct | gtcccctctt | aataacccta | gtcacagtct ccgcagattc |
| | | 901 ttgggatttg | ggggttttct | cccccacctc | tccactagtt | ggaccaaggt ttctagctaa |
| | | 961 gttactctag | tctccaagcc | tctagcatag | agcactgcag | acaggccctg gctcagaatc |
| | | 1021 agagcccaga | aagtggctgc | agacaaaatc | aataaaacta | atgtccctcc cctctccctg |
| | | 1081 ccaaaaggca | gttacatatc | aatacagaga | ctcaaggtca | ctagaaatgg gccagctggg |
| | | 1141 tcaatgtgaa | gccccaaatt | tgcccagatt | cacctttctt | cccccactcc ctttttttttt |
| | | 1201 tttttttttt | tgagatggag | tttcgctctt | gtcacccacg | ctggagtgca atggtgtggt |
| | | 1261 cttggcttat | tgaagcctct | gcctcctggg | ttcaagtgat | tctcttgcct cagcctcctg |
| | | 1321 agtagctggg | attacaggtt | cctgctacca | cgcccagcta | atttttgtat ttttagtaga |
| | | 1381 gacgaggctt | caccatgttg | gccaggctgg | tctcgaactc | ctgtcctcag gtaatccgcc |
| | | 1441 cacctcagcc | tcccaaagtg | ctgggattac | aggcgtgagc | cacagtgcct ggcctcttcc |
| | | 1501 ctctccccac | tgcccccccc | aactttttt | ttttttttat | ggcagggtct cactctgtcg |
| | | 1561 cccaggctgg | agtgcagtgg | cgtgatctcg | gctcactaca | acctcgacct cctgggttca |
| | | 1621 agtgattctc | ccacccccagc | ctcccaagta | gctgggatta | caggtgtgtg ccactacggc |
| | | 1681 tggctaattt | ttgtatttt | agtagagaca | ggtttcacca | tattggccag gctggtcttg |

| CHEMOKINE | GENBANK ACCESSION NO. | SEQUENCE |
|---|---|---|
| | | 1741 aactcctgac ctcaagtgat ccaccttcct tgtgctccca aagtgctgag attacaggcg |
| | | 1801 tgagctatca cacccagcct cccccttttt ttcctaatag gagactcctg tacctttctt |
| | | 1861 cgttttacct atgtgtcgtg tctgcttaca tttccttctc ccctcaggct tttttggggt |
| | | 1921 ggtcctccaa cctccaatac ccaggcctgg cctcttcaga gtacccccca ttccacttc |
| | | 1981 cctgcctcct tccttaaata gctgacaatc aaattcatgc tatggtgtga aagactacct |
| | | 2041 ttgacttggt attataagct ggagttatat atgtatttga aaacagagta aatacttaag |
| | | 2101 aggccaaata gatgaatgga agaattttag gaactgtgag aggggggacaa ggtgaagctt |
| | | 2161 tcctggccct gggaggaagc tggctgtggt agcgtagcgc tctctctctc tgtctgtggc |
| | | 2221 aggagccaaa gagtagggtg taattgagtg aaggaatcct gggtagagac cattctcagg |
| | | 2281 tggttgggcc aggctaaaga ctgggagttg ggtctatcta tgcctttctg gctgattttt |
| | | 2341 gtagagacgg ggttttgcca tgttacccag gctggtctca aactcctggg ctcaagcgat |
| | | 2401 cctcctggct cagcctccca aagtgctggg attacaggcg tgaatcactg cgcctggctt |
| | | 2461 cctcttcctc ttgagaaata ttcttttcat acagcaagta tgggacagca gtgtcccagg |
| | | 2521 taaaggacat aaatgttaca agtgtctggt cctttctgag ggaggctggt gccgctctgc |
| | | 2581 agggtatttg aacctgtgga attggaggag gccatttcac tccctgaacc cagcctgaca |
| | | 2641 aatcacagtg agaatgttca ccttataggc ttgctgtggg gctcaggttg aaagtgtggg |
| | | 2701 gagtgacact gcctaggcat ccagctcagt gtcatccagg gcctgtgtcc ctcccgaacc |
| | | 2761 cagggtcaac ctgcctgcca caggcactag aaggacgaat ctgcctactg cccatgaacg |
| | | 2821 gggccctcaa gcgtcctggg atctccttct ccctcctgtc ctgtccttgc ccctcaggac |
| | | 2881 tgctggaaaa taaatcttt aaaatagtaa aaaaaaaaaa aaa |
| Homo sapiens monocyte chemoattractant protein 1 (MCP-1) | x14768 | 1 ctaacccaga aacatccaat tctcaaactg aagctcgcac tctcgcctcc agcatgaaag |
| | | 61 tctctgccgc ccttctgtgc ctgctgctca tagcagccac cttcattccc caagggctcg |
| | | 121 ctcagccaga tgcaatcaat gccccagtca cctgctgtta taacttcacc aataggaaga |
| | | 181 tctcagtgca gaggctcgcg agctatagaa gaatcaccag cagcaagtgt cccaaagaag |
| | | 241 ctgtgatctt caagaccatt gtggccaagg agatctgtgc tgaccccaag cagaagtggg |
| | | 301 ttcaggattc catggaccac ctggacaagc aaacccaaac tccgaagact tgaacactca |
| | | 361 ctccacaacc caagaatctg cagctaactt attttcccct agctttcccc agacaccctg |
| | | 421 ttttatttta ttataatgaa ttttgtttgt tgatgtgaaa cattatgcct taagtaatgt |
| | | 481 taattcttat ttaagttatt gatgttttaa gtttatcttt catggtacta gtgtttttta |
| | | 541 gatacagaga cttggggaaa ttgcttttcc tcttgaacca cagttctacc cctgggatgt |
| | | 601 tttgagggtc tttgcaagaa tcattaatac aaagaattt ttttaacatt ccaatgcatt |
| | | 661 gctaaaatat tattgtggaa atgaatattt tgtaactatt acaccaaata aatatatttt |
| | | 721 tgtac |
| Homo sapiens RANTES | AF266753 (see also AW769950) | 1 atgaaggtct ccgcggcacg cctcgctgtc atcctcattg ttactgccct ctgcgctcct |
| | | 61 gcatctgcct ccccatattc ctcggacacc acaccctgct gctttgccta cattgcccgc |
| | | 121 ccactgcccc gtgcccacat caaggagtat ttctacacca gtggcaagtg ctccaaccca |
| | | 181 gcagtcgtct ttgtcaccg aaagaaccgc caagtgtgtg ccaacccaga gaagaaatgg |
| | | 241 gttcgggagt acatcaactc tttggagatg agctag |
| Homo sapiens B cell-attracting chemokine (BLC) | AJ002211 | 1 cagagctcaa gtctgaactc tacctccaga cagaatgaag ttcatctcga catctctgct |
| | | 61 tctcatgctg ctggtcagca gcctctctcc agtccaaggt gttctggagg tctattacac |
| | | 121 aagcttgagg tgtagatgtg tccaagagag ctcagtcttt atccctagac gcttcattga |
| | | 181 tcgaattcaa atcttgcccc gtgggaatgg ttgtccaaga aaagaaatca tagtctggaa |
| | | 241 gaagaacaag tcaattgtgt gtgtggaccc tcaagctgaa tggatacaaa gaatgatgga |
| | | 301 agtattgaga aaaagaagtt cttcaactct accagttcca gtgtttaaga gaaagattcc |
| | | 361 ctgatgctga tatttccact aagaacacct gcattcttcc cttatccctg ctctgggatt |
| | | 421 ttagtttttgt gcttagttaa atcttttcca gggagaaaga acttccccat acaaataagg |
| | | 481 catgaggact atgtaaaaat aaccttgcag gagctggatg gggggccaaa ctcaagcttc |
| | | 541 tttcactcca caggcaccct attntacact tgggggtttt gcnttctttn tttcntcagg |
| | | 601 ggggggggaaa gtttcttttg gaaantagtt nttccagttn ttaggtatta cagggttntt |
| | | 661 ttt |

Chemokines useful in the methods and compositions of the present invention include, but are not limited to, chemokines from mice, hamsters, dogs, cats, monkeys, rabbits, chimpanzees, and human. Preferred chemokines are of human origin. Nucleic acid sequences encoding suitable chemokines can be isolated from vertebrate, mammalian, human, porcine, bovine, feline, avian, equine, canine, as well as additional primate sources, etc.

DNA may be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions. Clones derived from cDNA will contain only exon sequences.

Whatever the source, the chemokine-encoding nucleic acid sequence can be molecularly cloned into a suitable vector.

In the molecular cloning of the gene from cDNA, cDNA is generated from totally cellular RNA or mRNA by methods that are well known in the art. The gene may also be obtained from genomic DNA, where DNA fragments are generated (e.g. using restriction enzymes or by mechanical shearing), some of which will encode the desired gene. Linear DNA fragments can be separated according to size using standard techniques, e.g, agarose and polyacrylamide gel electrophoresis and column chromatography.

Once the DNA fragments are generated, identification of the specific DNA fragment containing all or a portion of the chemokine gene may be accomplished in a number of ways.

A preferred method for isolating a chemokine gene is by the polymerase chain reaction (PCR), which can be used to amplify the desired chemokine sequence in a genomic or cDNA library or from genomic DNA or cDNA that has not been incorporated into a library. Oligonucleotide primers that hybridize to chemokine sequences can be used as primers in PCR.

Additionally, a portion of the chemokine (of any species) gene or its specific RNA, or a fragment thereof, can be purified (or an oligonucleotide synthesized) and labeled, the generated DNA fragments may be screened by nucleic acid hybridization to the labeled probe (Benton, W. and Davis, R., 1977, Science 196:180; Grunstein, M. and Hogness, D., 1975, Proc. Natl. Acad. Sci. U.S.A. 72:3961). DNA fragments with substantial homology to the probe will hybridize. Chemokine nucleic acids can be also identified and isolated by expression cloning using, for example, anti-chemokine antibodies for selection.

Alternatives to obtaining the chemokine DNA by cloning or amplification include, but are not limited to, chemically synthesizing the gene sequence itself from the known sequence or transcribing cDNA to mRNA which encodes the chemokine protein. Other methods are possible within the skill of the art and within the scope of the invention.

Once a clone has been obtained, its identity can be confirmed by nucleic acid sequencing (by any method well known in the art) and comparison to known chemokine sequences. DNA sequence analysis can be performed by any techniques known in the art, including, but not limited to, the method of Maxam and Gilbert (1980, Meth. Enzymol. 65:499–560), the Sanger dideoxy method (Sanger, F., et al., 1977, Proc. Natl. Acad. Sci. U.S.A. 74:5463), the use of T7 DNA polymerase (Tabor and Richardson, U.S. Pat. No. 4,795,699), use of an automated DNA sequenator (e.g., Applied Biosystems, Foster City, Calif.) or the method described in PCT Publication WO 97/15690.

Nucleic acids which are hybridizable to a chemokine nucleic acid (e.g., having sequence SEQ ID NO: 1), or to a nucleic acid encoding a chemokine derivative can be isolated, by nucleic acid hybridization under conditions of low, high, or moderate stringency (see also Shilo and Weinberg, 1981, Proc. Natl. Acad. Sci. USA 78:6789–6792).

Chemokines and their functional equivalents can be obtained by any method known in the art. Examples include recombinant expression methods, purification from natural sources, and chemical synthesis.

For example, chemokines can be obtained by recombinant protein expression techniques. For recombinant expression, a nucleic acid encoding the chemokine or its functional equivalent is inserted into an appropriate cloning vector for expression in a particular host cell. Many vector-host systems are known in the art. Examples include plasmids, cosmids, phagemids and modified viruses. The vector system should be compatible with the host cell used. Specific examples include bacteriophages, such as lambda derivatives; and plasmids, such as pBR322 or pUC plasmid derivatives or the BLUESCRIPT™ vector (Stratagene).

Insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and chemokine gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be accomplished prior to insertion into the cloning vector.

In specific embodiments, transformation of host cells with recombinant DNA molecules that incorporate the isolated chemokine gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

A nucleotide sequence coding for a chemokine or its functional equivalent, can be inserted into an appropriate expression vector, i.e., a vector which contains the necessary elements for the transcription and translation of the inserted protein-coding sequence. The necessary transcriptional and translational signals can also be supplied by the native chemokine gene and its flanking regions.

A variety of host-vector systems may be utilized to express the protein-coding sequence. These include, but are not limited to, mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination).

Expression of a nucleic acid sequence encoding a chemokine or its functional equivalent may be regulated by a second nucleic acid sequence so that the chemokine polypeptide is expressed in a host transformed with the recombinant DNA molecule.

Expression of a chemokine or its functional equivalent may be controlled by any promoter/enhancer element known in the art. Promoters which may be used to control expression include, but are not limited to, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift, et al., 1984, Cell 38:639–646; Ornitz, et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl, et al., 1984, Cell 38:647–658; Adames, et al., 1985, Nature 318:533–538; Alexander, et al., 1987, Mol. Cell. Biol. 7:1436–1444), mouse mammary tumor virus control region which is active in testicular, breast, lymphoid and mast cells (Leder, et al., 1986, Cell 45:485–495), albumin gene control region which is active in liver (Pinkert, et al., 1987, Genes and Devel. 1:268–276), alpha-fetoprotein gene control region which is active in liver (Krumlauf, et al., 1985, Mol. Cell. Biol. 5:1639–1648; Hammer, et al., 1987, Science 235:53–58; alpha 1-antitrypsin gene control region which is active in the liver (Kelsey, et al., 1987, Genes and Devel. 1:161–171), beta-globin gene control region which is active in myeloid cells (Mogram, et al., 1985, Nature 315:338–340; Kollias, et al., 1986, Cell 46:89–94), myelin basic protein gene control region which is active in oligodendrocyte cells in the brain (Readhead, et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason, et al., 1986, Science 234:1372–1378).

For example, a vector can be used that comprises a promoter operably linked to a chemokine-encoding nucleic acid, one or more origins of replication, and, optionally, one or more selectable markers (e.g., an antibiotic resistance gene).

In a specific embodiment, an expression construct is made by subcloning a chemokine coding sequence into the EcoRI restriction site of each of the three pGEX vectors (Glutathione S-Transferase expression vectors; Smith and Johnson, 1988, Gene 7:31–40). This allows for the expression of the chemokine product from the subclone in the correct reading frame.

The invention provides expression vectors comprising chemokine-encoding and/or antigen-encoding inserts. In a preferred aspect, the invention provides an expression vector comprising both chemokine-encoding and/or antigen-encoding inserts.

The expression vectors of the invention can be used to transform cells. Cells expressing the expression vectors can be identified by a variety of approaches known in the art. Examples include nucleic acid hybridization, identification of the presence or absence of "marker" gene functions, and expression of inserted sequences.

In the first approach, the presence of a target insert in an expression vector can be detected by nucleic acid hybridization using probes comprising sequences that are homologous to the target insert.

In a second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a target insert. For example, if the target insert is inserted within the marker gene sequence of the vector, recombinants containing the target insert can be identified by the absence of the marker gene function.

In a third approach, recombinant expression vectors can be identified by assaying for the chemokine product expressed by the recombinant. Such assays can be based, for example, on the physical or functional properties of the chemokine in in vitro assay systems, e.g., binding with an antigen and/or anti-chemokine antibody or a corresponding chemokine receptor.

Appropriate cells expressing the chemokine-encoding and/or antigen-encoding inserts can be administered to a subject as a live bacterial vaccine. Moreover, the cells may be killed and administered to a subject as a killed bacterial vaccine.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired.

Different host cells have characteristic and specific mechanisms for the translational and post-translational processing and modification (e.g., glycosylation, phosphorylation of proteins. Appropriate cell lines or host systems can be chosen to ensure the desired modification and processing of the foreign protein expressed. For example, expression in a bacterial system can be used to produce an unglycosylated core protein product. Expression in yeast can be used to produce a glycosylated product. Expression in mammalian cells can be used to ensure "native" glycosylation of a heterologous protein. Furthermore, different vector/host expression systems may affect processing reactions to different extents.

In other specific embodiments, the antigen and/or chemokine and/or functional equivalent can be expressed as a fusion, or chimeric protein product. A wide variety of combinations are possible, e.g., chemokine-antigen; chemokine-heterologous polypeptide; antigen-carrier protein; antigen-chemokine functional equivalent, etc. In a preferred aspect, the invention provides a fusion protein comprising an antigen and a chemokine. The fusion protein and the chemokine may suitably be separated by a spacer sequence, e.g., as described U.S. patent application Ser. No. 09/335,150. The fusion protein can be made by a variety of synthetic and recombinant methods known in the art. For example, nucleic acid sequences encoding the desired amino acid sequences can be ligated to each other in the proper coding frame, and the chimeric product can be expressed by methods known in the art. Alternatively, a chimeric product may be made by protein synthetic techniques, e.g., by use of a peptide synthesizer. In a specific embodiment, a chimeric protein containing all or a portion of a chemokine is joined via a peptide bond to all or a portion of an antigen against which immunity is desired.

The nucleic acids of the invention can be mutated in vitro or in vivo, to create and/or destroy translation, initiation, and/or termination sequences, or to create variations in coding regions. Any technique for mutagenesis known in the art can be used. Examples of suitable techniques include in vitro site-directed mutagenesis (Hutchinson, et al., 1978, *J. Biol. Chem* 253:6551), use of TAB linkers (Pharmacia), mutation-containing PCR primers, etc.

The experimentation involved in mutagenesis consists primarily of site-directed mutagenesis followed by phenotypic testing of the altered gene product. Some of the more commonly employed site-directed mutagenesis protocols take advantage of vectors that can provide single-stranded as well as double-stranded DNA, as needed. Generally, the mutagenesis protocol for such vectors is as follows. A mutagenic primer, i.e., a primer complementary to the sequence to be changed, but consisting of one or a small number of altered, added, or deleted bases, is synthesized. The primer is extended in vitro by a DNA polymerase and, after some additional manipulations, the now double-stranded DNA is transfected into bacterial cells. Next, by a variety of methods, the desired mutated DNA is identified, and the desired protein is purified from clones containing the mutated sequence. For longer sequences, additional cloning steps are often required because long inserts (longer than 2 kilobases) are unstable in those vectors. Protocols are known to one skilled in the art and kits for site-directed mutagenesis are widely available from biotechnology supply companies, for example from Amersham Life Science, Inc. (Arlington Heights, Ill.) and Stratagene Cloning Systems (La Jolla, Calif.).

Chemokine fragments can be obtained by proteolysis of the protein followed by purification using standard methods such as those described above (e.g., immunoaffinity purification).

6.4 Formulations and Methods of Administration

The formulations of the invention generally comprise, in association with a pharmaceutically acceptable carrier or excipient: (i) a chemokine or functional equivalent and an antigen;,(ii) a nucleic acid sequence encoding a chemokine or functional equivalent and a separate nucleic acid sequence encoding an antigen; (iii) a nucleic acid sequence encoding a chemokine or functional equivalent and also encoding an antigen; or (iv) combinations of any of the foregoing components. A nucleic acid encoding any of the chemokine (or functional equivalent therof) and/or the antigen is configured to express the sequence encoded thereby. The invention also provides pharmaceutical compositions comprising live or killed bacterial vectors transformed using the expression vectors of the invention.

Pharmaceutically acceptable components of the formulations (e.g., carriers and excipients) are well known in the art. Examples include physiological saline, buffered saline, dextrose, water, glycerol, ethanol, sterile isotonic aqueous buffer, and combinations thereof.

Where a live bacterial vector is used, an acceptable carrier is a physiologically balanced culture medium. The culture medium may, for example, comprise one or more stabilizing agents such as stabilized, hydrolyzed polypeptides, lactose, and the like.

In addition, if desired, the vaccine or composition preparation may also include minor amounts of auxiliary substances such as wetting or emulsifying agents, pH buffering agents, and/or adjuvants which enhance the effectiveness of the vaccine or composition.

Supplemental adjuvants may also be included in the compositions of the invention. Adjuvants include auxiliary agents which, when administered jointly with an antigen, increase the immunogenicity of the antigen or influence the quality of the immune response. Adjuvants are typically administered to improve the immunogenicity of an antigen, i.e., to increase antibody formation and/or to induce a stronger cell mediated immune response to the antigen.

Examples of suitable adjuvants include mineral gels (e.g., aluminum hydroxide); surface active substances (e.g., lysolecithin, pluronic polyols); polyanions; peptides; oil emulsions; and alum. See Derek T. O'Hagan, *Vaccine Adjuvants: Preparation Methods and Research Protocols*, Humana Press, 2000, for further examples. The effectiveness of an adjuvant may be determined by comparing the induction of antibodies directed against a composition of the invention composition in the presence and in the absence of the adjuvant. Specific methods are discussed in O'Hagan supra.

The composition can take any of a variety of forms known in the art, e.g., liquid solution, suspension, emulsion, microemulsion, tablet, pill, capsule, sustained release formulation, powder, etc.

Oral formulations suitably comprise standard excipients such as pharmaceutical grades of mannitol, lactose, starch, magnesium stearate, sodium saccharine, cellulose, magnesium carbonate, and the like.

Polypeptide components of the compositions of the invention may be formulated as neutral or salt forms. Pharmaceutically acceptable salts and methods for making them are known in the art. Examples include acid addition salts (formed with free amino groups of the peptide). Acid addition salts may be prepared using inorganic acids (e.g., hydrochloric or phosphoric acids) or organic acids (e.g., acetic, oxalic, tartaric, maleic, and the like). Salts formed with free carboxyl groups may also be derived from inorganic bases, e.g., sodium potassium, ammonium, calcium, or ferric hydroxides, and such organic bases as isopropylamine, trimethylamine, 2-ethylamino ethanol, histidine, procaine and the like.

Polypeptide components of the compositions of the invention may also be constructed as univalent, divalent or multivalent polypeptides. The polypeptides may contain multiple copies of the same antigen species or multiple (i.e., two or more) antigen species. Similarly, the polypeptides may contain multiple copies of the same chemokine species or multiple (i.e., two or more) chemokine species. The polypeptides may also comprise one or more chemokine species in a fusion polypeptide with one or more antigen species.

The compositions of the invention are suitably administered to a subject in an amount sufficient to elicit an enhanced immune response. The compositions of the invention are also suitably administered to a subject in an amount sufficient to enhance an ongoing immune response. The compositions of the invention are preferably administered to a subject in an amount sufficient to cause an immunizingly effective response.

The precise dose of the active components of the composition to be employed in the formulation will depend on a variety of factors known to those of skill in the art. For example, factors to be considered include the route of administration and the nature of the subject to be immunized. The effect of such factors, and other factors known in the art, is readily determined by one of skill in the art according to standard clinical techniques. Effective doses of the active components of the compositions of the present invention may also be extrapolated from dose-response curves derived from animal model test systems.

The invention also provides a pharmaceutical pack or kit comprising one or more containers comprising at least one antigen component (polypeptide and/or antigen-encoding nucleic acid) and at least one chemokine component (polypeptide and/or chemokine-encoding nucleic acid) for preparing a vaccine composition of the invention. A notice can be associated with such container(s). The notice is preferably in a form prescribed by a governmental agency regulating the manufacture, use or sale of pharmaceuticals or biological products. Further, the notice may reflect approval by the agency for manufacture, use or sale for human administration.

Generally, the ingredients of the compositions of the invention are supplied either separately or mixed together in unit dosage form. An example of the former is a dry lyophilized powder or water free concentrate in a hermetically sealed container, such as an ampule or sachette indicating the quantity of active agent. Where the composition is administered by injection, an ampoule of sterile diluent can be provided so that the ingredients may be mixed prior to administration.

In a specific embodiment, at least one antigen and at least one chemokine of the invention is provided in a first container (or a fusion polypeptide comprising both antigen and chemokine or functional equivalent), and a second container comprises diluent consisting of an aqueous solution of 50% glycerin, 0.25% phenol, and an antiseptic (e.g., 0.005% brilliant green).

A variety of known methods for administering vaccines may be used to administer the compositions and formulations of the invention. These include but are not limited to: oral, intradermal, intramuscular, intraperitoneal, intravenous, subcutaneous, intraosseous, intranasal routes, and via scarification (scratching through the top layers of skin, e.g., using a bifurcated needle). The nucleic acid vaccines of the invention can be administered by any method known in the art for delivery of DNA to subject.

6.5 Assays

The activity of the compositions of the present invention can be validated by monitoring the immune response in test animals following immunization with a composition comprising a first component selected from the group consisting of: (i) an antigen against which an immune response is desired in the subject; and (ii) a nucleic acid encoding the antigen; and a second component selected from the group consisting of: (i) a chemokine selected from the group consisting of RANTES, MCP-1, MDC and BLC, or a functional equivalent of said chemokine; and (ii) a nucleic acid encoding the chemokine. As previously discussed, the chemokine and antigen components may also be administered as components of separate compositions, in any chronological order.

The response of the test animals can be compared to a response in control animals immunized with a corresponding antigen alone. Where the chemokine is provided as a component of a fusion polypeptide which also comprises the antigen, a suitable control will also include animals administered with a corresponding chemokine and a corresponding antigen not contained in a fusion polypeptide. Other controls will be apparent to persons of skill in the art.

An immune response is indicated, for example, by generation of a humoral (antibody) response and/or cell-mediated immunity. Test animals may include mice, hamsters, dogs, cats, monkeys, rabbits, chimpanzees, etc., and eventually human subjects. Assays for humoral and cell-mediated immunity are well known in the art. The immune response of the test subjects can be analyzed by various approaches well known in the art. Examples include testing the reactivity of the resultant immune serum to the antigen of the composition or fusion polypeptide, as assayed by known techniques (e.g., immunosorbant assay (ELISA), immunoblots, radioimmunoprecipitations, and the like).

Methods of introducing the composition into animals used in assays of the present invention may include oral, intracerebral, intradermal, intramuscular, intraperitoneal, intravenous, subcutaneous, intraosseous, intranasal or any other standard routes of immunization.

As one example of suitable animal testing, compositions of the present invention may be tested in mice for the ability to enhance an antibody response to an antigen component of the composition and/or a delayed-type hypersensitivity (DTH) response, measured by an increase in footpad swelling after inoculation in the footpad of the test animal. These measurements can then be compared to corresponding measurements in control animals. As an example, BALB/c mice may be used as test animals.

Serum samples may be drawn from the mice after the final inoculation (for example every one or two weeks after inoculation). Serum can be analyzed for antibodies against the antigen using known methods in the art, e.g., using an ELISA. DTH responses to the antigen may be measured after the final inoculation (e.g. within 1–7 days). An increase in the serum titer of antibodies recognizing the antigen and/or an increase in footpad swelling in the animals receiving the composition of the invention as compared to the serum titer of the control animals, indicates that composition enhances the immune response to antigen.

7. EXAMPLES

The following empirical work was performed in support of the application:

7.1 Plasmids (recombinant), Proteins and Immunization Regimen

The murine chemokines RANTES, MCP-1, MDC and BLC were cloned into the pcDNA3 expression vector (Invitrogen, Inc., San Diego, Calif.) driven by a CMV promoter (see miscellaneous). Plasmids for injection were produced in E. coli strain DH5cc and prepared by EndoFree Giga kit (Qiagen, Santa Clara, Calif.). The preparation was followed by sodium acetate precipitation until an endotoxin level of 0.5 EU/ml, detected by limulus amoebocyte lysate assay (BioWhittaker, Walkersville, Md.).

For the DNA vaccinations, 6–8 weeks old female Balb/c mice (Charles River Laboratories, Wilmington, Mass.) were injected intramuscularly (i.m.) into each quadricep (tibialis anterior muscle). Mice are anesthetized prior to each injection with 1 $\mu$l/g of a mix of 1:1 Ketamine and Xylazine to which is added 0.015 mg/ml of Butorphenol. Four mice per group were injected with 100 $\mu$g of plasmid DNA, dissolved in 50 $\mu$l TE buffer into each leg, encoding to equal amounts one of the chemokines or the vector pcDNA3.1 and gp120 or gp160, respectively (table 2a). The first DNA injection preceded (11 days) an i.m. injection of 50 $\mu$l snake cardiotoxin (Sigma, St Louis, Mo.) in each quadricep. The three injections were separated by two weeks and serum samples were taken prior to each injection by technicians of the animal facility and three weeks after the final injection (see FIG. 2a). All animals were housed according to the guidelines of the National Institute of Health and the University of Maryland.

TABLE 2A

DNA immunization groups. Injection of the different plasmid combinations as performed for both assays, with gp120 and gp160 as antigen, intramuscularly under anesthesia in a volume of 50 µl phosphate buffered saline.

| DNA Vaccination | Group | Immunization with pcDNABalgp160 | Immunization with pcDNABalgp120 |
|---|---|---|---|
| Vector alone | 1 | PcDNA3.1 (100 µg per leg and injection) | PcDNA3.1 (100 µg per leg and injection) |
| Antigen alone | 2 | PcDNABalgp160 + pcDNA3.1 (1:1, 50 µg of each construct per leg and injection) | PcDNABalgp120 + pcDNA3.1 (1:1, 50 µg of each construct per leg and injection) |
| Antigen + BLC | 3 | PcDNABalgp160 + pcBLC (1:1, 50 µg of each construct per leg and injection) | PcDNABalgp120 + pcBLC (1:1, 50 µg of each construct per leg and injection) |
| Antigen + MCP-1 | 4 | PcDNABalgp160 + pcMCP-1 (1:1, 50 µg of each construct per leg and injection) | PcDNABalgp120 + pcMCP-1 (1:1, 50 µg of each construct per leg and injection) |
| Antigen + MDC | 5 | PcDNABalgp160 + pcMDC (1:1, 50 µg of each construct per leg and injection) | PcDNABalgp120 + pcMDC (1:1, 50 µg of each construct per leg and injection) |
| Antigen RANTES | 6 | PcDNABalgp160 + pcRANTES (1:1, 50 µg of each construct per leg and injection) | PcDNABalgp120 + pcRANTES (1:1, 50 µg of each construct per leg and injection) |

TABLE 2B

Protein immunization groups. Groups of four animals were injected in the base of the tail with different concentrations of mMDC 18 h prior to an injection of ovalbumine, both in 15 µl of a phosphate buffered saline.

| Protein vaccination | Injection of the chemokine murine MDC | Injection of the antigen, 18 h later |
|---|---|---|
| 1 | 3 µg mMDC (in 15 µl PBS) | 10 µg ovalbumine (in 15 µl PBS) |
| 2 | 1 µg mMDC (in 15 µl PBS) | 10 µg ovalbumine (in 15 µl PBS) |
| 3 | 0.3 µg mMDC (in 15 µl PBS) | 10 µg ovalbumine (in 15 µl PBS) |
| 4 | 0.1 µg mMDC (in 15 µl PBS) | 10 µg ovalbumine (in 15 µl PBS) |
| 5 | 0.03 µg mMDC (in 15 µl PBS) | 10 µg ovalbumine (in 15 µl PBS) |
| 6 | 15 µl PBS alone | 10 µg ovalbumine (in 15 µl PBS) |
| 7 | 15 µl incomplete Freund's adjuvant | 10 µg ovalbumine (in 15 µl PBS) |

For the protein injections, different concentrations of recombinant murine MDC (R&D Systems, Minneapolis, Minn.) ranging from 0 to 3 µg dissolved in 15 µl phosphate buffered saline (PBS) (Biofluids Division, Biosource International, Rockville, Md.) were injected into different groups of mice (n=4). One group recieved 15 µl incomplete Freund's adjuvant (IFA). An injection site at the base of the tail was identified with a water resistant marker. Chemokine was injected to different concentrations (table 2b) at the marked location, followed 18 h later by injection of 10 µg ovalbumine (chicken egg, grade V; Sigma, St Louis, Mo.) in a total volume of 15 µl PBS. This injection protocel was performed at day 1, 14, 21 and 28 (see FIG. 2b). One week after final injection mice were bled and sacrificed by vertebral dislocation. Injections were performed by or under supervision of a certified veterinarian.

7.2 Serum Antibody Assay

To monitor the development of the specific Ab response against gp120 and gp160 in the DNA vaccination assays and the effect of the co-immunized chemokines BLC, MCP-1, MDC and RANTES on the induced response, the immunized mice were bled retroorbitally on the morning of the days of injection (week 0, 2, 4) and three weeks post-final injection (week 7) and serum samples were analyzed by ELISA. Briefly, a ninety-six well Maxisorp ELISA plate (Nunc, Naperville, Ill.) was coated over night with 100 µl of 2 µg/ml anti-HIV-1$_{BaL}$ gp120 capture Ab (D7234, International Enzymes, Inc, Falibrook, Calif.) at room temperature, washed with PBS-0.5% Tween-20, blocked with 200 µl of 5% skimmed milk powder in PBS for 1 h and after another washing step, loaded with 2 µg/ml rgp140 for another hour. The plate was again washed and 100 µl/well of the heat-inactivated serum samples (30 minutes at 56° C.) were added. Serial dilution were also made in PBS containing 2% skimmed milk powder and 5% sheep serum yielding a final volume of 100 per well. Following one hour incubation, the plate was washed, and incubated with a 1/2000 dilution of horseradish peroxidase conjugated affinity-purified and serum adsorbed goat anti-mouse secondary Ab (Kierkegaard&Perry Laboratories (KPL), Gaithersburg, Md.) for 1 h. The plate was washed again and developed with 100 µl tetramethylbenzidine (TMB) (KPL, Gaithersburg, Md.) for 20 minutes, stopped with 50 µl 1N $H_2SO_4$ and analyzed at 450 nm (absorption at 570 nm) with a Victor plate reader (Wallac, Turku, Finland). Subtyping of the Abs in order to determine the Th-type of the immune response was conducted using the same protocol, apart from the replacement of the secondary Ab with either HRP conjugated IgG1or IgG2a goat anti-mouse Abs (KPL, Gaithersburg, Md.).

For the MDC protein vaccination assay 96-well microliter plates (Nunc, Naperville, Ill.; flat bottom plates) were coated over night at 4° C. with 100 µl of 1 µg/ml chicken ovalbumine (Sigma, St Louis, Mo.) in PBS and blocked with 2% skimmed milk powder (blotto). After subsequent washing with 0.5% PBS-Tween20, 100 µl of a solution of 1% blotto and serum, serially diluted further in 1% blotto, were added to the plate and incubated for 15 hour at room temperature. The plates were washed and HRP-conjugated goat-anti-mouse IgG (KPL, Gaithersburg, Md.) was added at a concentration of 1 µg/ml, diluted in 2% blotto and incubated at room temperature for 1 hour. After another washing step, 100 µl TMB was added and incubated for 20 minutes at room temperature. The reaction was stopped by adding 50 µl of 1N $H_2SO_4$. After approximately 5 minutes, the OD value was determined on a plate reader (Wallac, Turku, Finland) at 450 nm.

7.3 IFN-γ ELISpot and Cytokine Assays

ELISpot assays were performed as published (Miyahira, Y., et al., 1995). Briefly, at 60 days after the 3$^{rd}$ injection (see FIG. 2a) mice are sacrificed and spleens are removed aseptically and placed in PBS. After mincing the spleens between two frosted glass slides, splenocytes were pooled (n=4) to obtain a single cell suspension. In order to remove erythrocytes, splenocytes were treated with 5 ml ACK lysis buffer (Sigma, St Louis, Mo.) and incubated for 5 minutes at 37° C. Cells were then washed in complete RPMI, counted and maintained in culture in T25 flasks starting at a concentration of 5×10$^6$/ml in 10 ml complete RPMI for 6 days in the presence of an equal number of P815 cells, which had been irradiated with 10 Rad in a GammaCell irradiator.

To generate appropriate stimulator cells, P815 cells are pulsed at day 6 with 10 μg/ml relevant peptide V3 peptide for 2 h at 37° C. They are then added to 1×10⁵ effector splenocytes at a ratio of 1:3 in a total volume of 270 μl complete RPMI per well with 10% FBS and 50 U/ml human II-2 (Genzyme Molecular Oncology, Framingham, Mass.) in Millipore HA ELISpot in Multiscreen 96-Filtration-ELISpot plates (Millipore, S.A., Molsheim, France), which had been coated overnight at room temperature with 100 μl of 5 μg/ml anti-INF-γ (clone #18181D, Pharmingen, San Diego, Calif.) in PBS, washed with PBS and blocked with 200 μl complete RPMI for >30 minutes at 37° C. As negative control, effector splenocytes were cultivated in complete RPMI only, whereas the positive control contained splenocytes from mice who were intraperitoneally injected 7 days pior to spleen removal with 5×10⁶ P815 cells. Those have further been pulsed for 2 h with V3-peptide. The effector cells were co-cultured with these pulsed stimulator cells at the same ratio and schedule as mentioned above. The ELISpot plate was incubated for 15–24 h at 37° C., then washed 2× with PBS, 1× with dH20 and another 2× with PBS-Tween20 (0.05%). The plate was incubated with 100 μl anti-INF-γ (clone #18112D, Pharmingen, San Diego, Calif.) at a concentration of 2 μg/ml in 0.05% PBS-Tween20 and 1% FBS for 2 h at room temperature. The plate was washed 4× with 0.05% PBS-Tween20 and 100 μl of freshly 1/2000 in PBS-Tween20 and 1% FBS diluted ExtrAvidin-alkaline phosphatase (product number: E-2636, Sigma, St Louis, Mo.) was added per well, followed by a 2 h. incubation at room temperature. The plates were then washed 3× with 0.05% PBS-Tween20 and 200 μl of freshly prepared BCIP/NBT (5-Bromo-4-chloro-3-indolyl Phosphate/Nitroblue Tetrazollum) substrate buffer (product number: B5655, I tablet yields 10 ml substrate, Sigma, St Louis, Mo.), dissolved in dH20, was added to each well. Once major spots developed (between 5 and 30 minutes) the reaction was stopped by washing with $dH_2O$. The supporting manifold was removed and the plate air-dried. The spots are counted using a dissection light microscope.

To discriminate the Th pattern of the immune response induced by the vaccine and the coadministered chemokines, 150 μl supernatant from the flasks containing the effector splenocytes in complete RPMI was taken at day 3 and examined for cytokine expression by ELISA (R&D Systems, Minneapolis, Minn.) according to the manufacturer's protocols. They were tested for murine Th1-type cytokine IFN-γ and Th2-type cytokine IL-4 and also for MIP-1α.

7.4 Results

The effect of chemokines on the immune response against different antigens in DNA vaccination studies was investigated using HIV-1 glycoproteins gp120 and gp160, two of the antigens currently studied as potential HIV vaccines. Studies were initiated to explore whether select plasmid-expressed chemokines, coadministered with a DNA expression vector encoding for gp120 or gp160, may enhance or modulate immune responses in a mouse model. One hundred μg of DNA expression vectors encoding for the antigen, either HIV-1$_{BaL}$ gp120 or HIV-1$_{BaL}$ gp160, were injected intramuscularly (i.m.), together with equal amounts of the murine chemokines, BLC, or MCP-1, or MDC, or RANTES. Control vector DNA was injected as a control. The generation of antigen-specific antibody response in serum was monitored, as a marker of humoral immune response. Specifically, capture ELISAs using the recombinant protein gp140 were performed. The Th-profile of the immune response was investigated by determination of the IgG1:IgG2a-ratio, pre- and post-immunization. The expression of select cytokines, such as IL-4 and INF-γ, but also MTP-1α, were also used as markers of Th status. Antigen-specific ELISpot assays for INF-γ secreting cells were performed in a mixed lymphocyte assay, which serve as marker of CTL activity.

In addition, a protein vaccination assay with ovalbumine, was conducted with different amounts of MMDC, administered 18 h prior to antigen injection, and its adjuvant properties evaluated.

The results herein reflect a study of the modulation of the adaptive immune response, to antigens administered along with immuno-modulating agents, in our case chemokines, by measuring markers of humoral and cell mediated immunity. The initiation of the antigen-specific immune response is a complex process involving coordinated expression of cytokines, chemokines, as well as their receptors (Foxman, E. F., 1997) and the specific, identifiable roles of select chemokine is the basis of this study.

Different chemokines are associated with different Th profiles and their specific role in immune induction and modulation, when coadministered with HIV-1$_{BaL}$ gp120- or gp160 DNA was investigated. (For the different injection groups refer to table 2a). In particular, the differences of the humoral responses elicited by the antigens alone and when coadministered with BLC, MCP-1, MDC or RANTES are compared. Further, the influence of the chemokine-antigen codelivery on the cell-mediated immunity (CMI) is investigated. According to their chemoattractant properties, it was expected that whereas MCP-1 and RANTES induce a stronger Th1-type response (Kim, J. J., et al 1998; Xin, K. G., 1999), MDC and especially BLC would induce a Th2-biased response. Furthermore, it is known that apart from the delivery route and site, the nature and dose of the antigen and the adjuvant formulation, as well as the regimen, strongly modulate the immunologic reaction.

The humoral response against gp120, when injected alone was substantially higher than the vaccination with gp160 alone, when following the same infection regimen, which indicates that the use of a soluble antigen modulates the immune response that leads to an increased Ab production. This result demonstrates the significance of the form of the antigen used. Furthermore, a significant increase in the antigen-specific Ab titer was detected after the second injection for both the soluble antigen gp120 as well as the membrane-bound antigen gp160, but this changed after the third injection. Both titers declined. This finding suggests the importance of the regimen and informs future vaccination strategies.

Regarding the effect contributed by the chemokines, we obtained a complex picture. Whereas all the chemokines, except for RANTES, increased antibody titers, and therefore showed an adjuvant effect when injected two times together with gp120, there was no such effect in the case of gp160. Indeed, there was no chemokine that induced a higher titer at any time point of the regimen as gp160 alone. For gp120, the B cell attracting chemokine BLC induced a strong and enhanced humoral response, as measured at the day of the 3rd injection, compared to when the antigen was injected alone and the titer with gp160 approached the titer of gp160 alone, although only after 3 injections.

Moreover, whereas the titer increased further for the other chemokine-coimmunized groups, as well as the group with gp120 alone, it declined in the case of BLC. When gp160 is used as an antigen, we observed that the tendencies go in a different direction. Antibody titers increase when BLC is coinjected with antigen and decline when other chemokines are used, as compared to antigen alone.

Barouch, D. H. (1998) made a similar observation: the coadministration of cytokine and gp120-DNA decreased gp120-specific Ab titers. Another factor that might have contributed to the decline in the antibody titer could be the fact that cells, after being attracted, are quickly desensitized either only to the same chemokine (homologous desensitization), but might be non-responsive to other chemokines as well (homologous desensitization) (Kim, C. H. and Broxmeyer, H. E., 1998).

Therefore we consider that the number of injections, when an increase in the humoral response is desired, depends on the chemokine used as adjuvant, as well as the nature of the antigen.

The surprisingly high Ab titer of the Th1-associated MCP-1 injected group in the gp160 immunization assay after only 2 injections compared to BLC, as 'positive control,' suggests that this chemokine has a primary role in the establishment of the immune response.

Taken together, when an enhanced humoral immune response is desired, soluble antigens should be used and BLC is useful as a potent adjuvant to minimize the number of necessary injections.

The protein vaccination revealed MDC as a potent inducer of the humoral immune response. In this study, the base of the tail as the site of injection was used, in order to obtain a high local concentration of chemokine. This route allowed the trapping of both the antigen, and the chemokine within the fibrous tissue of the tail. To further enhance the benefit deriving from attracting cells to the site of injection, injection of the chemokine was performed 18 hours prior to the antigen injection. The results show the immune-enhancing properties of MDC, which significantly increased antigen-specific antibody titers. This observation is consistent with a conclusion that, due to the important role of MDC in inducing immune response, future immunosuppressive therapy protocols will include MDC antagonists.

When looking at the influence of the chemokines and their immuno-modulating effects, it was established by Ab isotype determination, that BLC is associated with a strong Th2 profile, regardless of whether it was used in conjunction with gp120 or gp160. This is deduced from the high IgG1:IgG2a ratios, shown in FIG. 6. Therefore, when a strong humoral response is desired, BLC can be the adjuvant of choice, ensuring antigen-specific reactions, in contrast to most other, mitogenic adjuvants. However, it is very likely that together with other adjuvant formulation, an increase in the antibody titer can be attained.

The investigation of Th-type related cytokine expression did not provide clear-cut results. In the cases of INF-γ (Th 1 type) and IL-4 (Th 2 type), the amount of cytokine expressed in tissue culture supernatants were too low, except when RANTES was coinjected with the antigen: in this group IFN-γ was present in detectable levels. In contrast, detectable levels of MIP-1α were observed in all the groups, although only the group coinjected with RANTES expressed MIP-1α levels higher than these observed in the group injected with the antigen alone. The release of MIP-1α in all the other groups was lower than that the vector-injected group, possibly reflecting some conditioning effect of the immunization procedure on the production of this chemokine. The fact that MIP-1α was strongly induced when the antigen was coinjected with RANTES, has importance in HIV vaccine applications, where induction of HIV-suppressive chemokines, such as MIP1α, can be beneficial in establishing protection.

Analyzing the effects of the chemokine coimmunization on the cellular response, as studied by ELISpot assay, we showed that MCP-1 and RANTES induced the strongest INF-γ response, whereas the cellular response was of the group coimmunized with BLC and MDC was inferior to the group immunized with antigen alone. The comparison of the results, obtained from the isotype determination (compare ratios indices of FIG. 5) and the strengths of the humoral response, provide a result, which could be interpreted as followed: A strong humoral response is accompanied with Th2 pattern and repressed cellular response, and vice versa. According to those findings, when it is desirable to induce Th1 type-specific responses, for combating intracellular pathogens, such as viruses, formulations containing, for example, MCP-1 can be advantageously employed.

Our results are consistent with the conclusion that chemokines can drive immune responses in relation to their associated Th-type and can serve as immunologic adjuvants. In addition, chemokines, which function both as adjuvants and as HIV-inhibitors, such as MDC, are especially suitable for use in the formulation of an HIV vaccine.

7.5

7.5.1 Humoral Response After DNA Immunization with pcDNABaLgp120 or pcDNABaLgp160, Along with Plasmids Expressing mBLC, mMCP-1, mMDC, or mRANTES (A) and After Protein Immunization with Ovalbumine and mMDC (B)

(A) DNA immunization: The humoral immune response was studied by capture ELISAs using recombinant protein gp140. At week four, antibody titers were well above background. While the gp120 construct induced an endpoint titer of 27000, the titers of gp120 coinjected with BLC, MDC, MCP-1, and RANTES were 132000, 112000, 31500 and 16500 respectively. Therefore, the co-administration of gp120 and BLC, enhanced the antibody response. A similar effect, although less pronounced, was observed in the case of MCP-1. MDC had marginal enhancing effect, while RANTES appears to have a negative effect. This trend was diminished at week 7.

The chemokines BLC and MCP-1 failed to further increase antibody titers as compared to the antigen alone group, whose antibody titers increased dramatically, relative to the chemokine co-immunized groups (FIG. 3a). This observation is consistent with the conclusion that the coadministration of chemokines induces a faster response and hence the peak is achieved earlier than in the case of immunization with the antigen alone.

MDC retained marginal adjuvant effect compared to the group injected with gp120 alone, suggesting a delayed effect of this chemokine as compared to the others. In the case of the immunization with gp120 alone, the overall Ab titer was about 15 to 20-fold higher compared to the immunization with gp 160 (FIGS. 3a and b). The endpoint antibody titer using $gp160_{BaL}$ alone was 6800 at week 4 and 6250 at week 7. We reasoned that this difference in antibody titers may be due to the increased uptake and hence more efficient presentation of the soluble form of the envelope protein, verses the membrane-bound form gp 160.

In the case of the immunization with pcDNABaLgp160 (FIG. 3b), performed with a similar regimen, different results were obtained. There was no immuno-enhancing effect due to the co-administration of chemokines. The total Ab titer against gp160 was low at week 2, rising sharply at week 4. The strongest increase however was not for the groups, which were co-immunized with the chemokine expression plasmids, but for the antigen alone. In the chemokine-coimmunized groups, at week 4, the day of the 3" immunization, the highest Ab titer, was obtained from the group, which recieved MCP-1 along with the antigen pcDNABaLgp160. In both immunization protocols with gp120 and gp160, RANTES seemed to negatively affect antibody titers, as compared to the control antigen. This suggests that RANTES is involved in some phenomenon of immune suppression. In general, BLC seemed to have the overall best activity in terms of antibody response enhancement although MDC triggered a delayed but substantial response in conjunction with gp120.

(B), Protein vaccination: It was shown that MDC markedly enhanced the immune response against ovalbumine and that the relation was dose-related (FIG. 4). We established a 67-fold increase in the immune response when 3 $\mu$g of mMDC was injected 18 h prior to ovalburnine injection in the same spot 4x in the base of the tall, compared to the control, injected with PBS and antigen alone. This increase in the immune response supports the idea of using MDC as an adjuvant, especially in protein formulations.

7.5.2 Influence of the Chemokine Coimmunization on the Polarization of the Immune Response In order to verify the Th profile known to be associated to each chemokine used in this experiment, the ratio of antigen specific IgG1 to IgG2a Abs and the cytokine expression pattern was investigated. The ratio between IgG1and IgG2a isotypes is directly related to the Th profile of an immune response. A high ratio or the predominance of the IgG1 isotype reflects a Th2 pattern, what again is related to a stronger humoral response, whereas a Th1 pattern is related to a response biased towards the cellular mediated immunity (FIG. 5b).

1) The Ratio of IgG1:IgG2a

ELISAs to establish IgG1:IgG2a isotype were performed as capture assays with serum samples collected at week 7 and compared to those of the prebleed (at week 0). The data obtained here confirmed the properties associated to each chemokine. According to the data obtained with the gp120 immunization, BLC induced the highest IgG1:IgG2a ratio, whereas the other chemokines did not significantly affect this parameter (FIG. 5a).

When gp160 immunization was used as immunogen, IgG1:IgG2a ratios were not significantly changed when pcDNABaLgp160 was coadministered with BLC (values were 100 and 103.2, respectively. When MDC was coinjected, the IgG1:IgG2a ratio was about half of that obtained using antigen alone. Injecting the antigen together with MCP-1 or RANTES, induced very low IgG1:IgG2a ratio, of 5 and 4.4, respectively. When gp120 was used for immunization, BLC caused a dramatic increase in the ratio IgG1:IgG2a, significantly higher than that of gp120 alone (448.4 with BLC, as compared to 36.5 of antigen alone). Coinjection of MCP-1, MDC, or RANTES with gp120 did not significantly alter IgG1:IgG2a, as compared to antigen alone.

11) Pattern of Cytokine Expression

ELISA assays were conducted to investigate the cytokines expression pattern of the mice immunized with the different chemokines, or the antigen alone. In order to do so, the mice immunized with the gp160 expressing construct were sacrificed at week 13, their spleens removed, pooled and the splenocytes cultured in presence of V3 peptide for three days in RPMI with 10% FBS (for more detailed description refer to the ELISpot assay above). At day three the levels in the tissue culture supernatants of INF-$\gamma$ (a Th1 cytokine, I1-4 (a Th2 cytokine) and MIP-1$\alpha$ (a chemokine of potential importance in HIV immunization, since it has HIV-suppressive properties) were analyzed with commercial ELISA kits according to the manufacturer's protocols.

I1-4 and IFN-$\gamma$ concentrations in tissue culture supernatant were below the detection limit. Only in RANTES co-immunized animals the concentrations of INF-$\gamma$ were at the detection threshold. Surprisingly, when expression of MIP-1$\alpha$ was examined, relatively high levels of this chemokine were found in the RANTES co-immunized animals. (FIG. 6).

8. REFERENCES

Various references are cited herein, the entire disclosure of each such reference is incorporated by reference in their entireties, as are the following references:

AIDS Alert (1998). Controversial HIV vaccine enters phase III trials amid skepticism. 13: 12

Allison AC (1997). Inununological Adjuvants and their modes of action. Archivum Immunologiae et Therapiae Experimentalis. 45:141–147

Baggiolini M and Moser B (1997). Blocking chemokine receptors. I Exp Med 186: 1189–91

Baggiolini M, Dewald B, Moser B (I 997). Human chemokines: an update. Annu Rev Immunol 15: 675–705

Barnett S W, Klinger J M, Doe B, Walker C M, Hansen L, Duli@ge A-M and Sinangil F M (1998). Prime-Boost immunization strategies in HIV. AIDS Reseach and Human Retroviruses 14: S299–S309

Barnett S W, Klinger J M, Doe B, Walker C M, Hansen L, Duli@ge A M, Sinangil F M (1998). Frime-boost immunization strategies against HIV. AIDS Res Hum Retroviruses October 14 Suppl 3: S299–309

Barouch D H, Santra S, Steenbecke T D, Zheng X X, Perry H C, Davies M-A, Freed D C, Craiu A, Strom T B, Shiver J W and Leivin N L (1998). Augmentation and suppression of immune responses to an HIV-1 vaccine by plasmid cytokine/ig administration. J Immunol. 161:1875–1882

Behr-inget D, Kresin V, Henschier R, Merteismann R, Lindemann A Br (I 997). Cytokine and chemokine production by CD34$^+$ haemopoietic progenitor cells: detection in single cells.J Haematol April;1997(1):9–14 Department of Haematology/Oncology, University of Freiburg, Germany.

Bochner B S, Bickel Calif., Taylor M L, MacGlashan D W Jr, Gray P W, Raport C J, Godiska R (1999). Macrophage-derived chemokine induces human eosinophil chemotaxis in a CC chemokine receptor 3- and CC chemoikine receptor 4-independent manner. J Allergy Clin Immunol Mar 103:3 Pt 1 527–32

Bruehl P et al., Kerschbaum K, Eibl M M, Mannhalter J W (I 998). An experimental prime-boost regimen leading to HIV type I-specific mucosal and systemic immunity in BALB/c n-@ce. AIDS Research and Human Retroviruses 14(5): 401–407

Burton D R and Moore J P (1998). Why do we not have an HIV vaccine and how can we make one? Naure Medicine Vaccine Supplement 4(5): 495–498

Campbell J J, Foxman E F, Butcher E C (1997). Chemoattractant receptor cross talk as a regulatory mechanism in leukocyte adhesion and migration. Eur J Immunol 27: 2571–78

Chen J D, Bai X, Yang A G, Cong Y, and Chen S Y (1997). Inactivation of HIV-1 chemokine co-receptor CXCR4 by a novel intrakine strategy. Nature Medicine 3:1110–1116

Chun S, Daheshia M, Kuklin N A and Rouse B T (1998). Modulation of viral immunoinflammatory responses with cytokine DNA administered by different routes. J Virol. 72(7): 5545–5551

Cohen A D, Boyer I D, Weiner D B (1998). Modulating the immune response to genetic immunization.

Connor R I et al (1998). Immunological and virological analyses of persons infected by human immunodeficiency virus type I while participating in trials of recombinant gp120 subunit vaccines. I Virol 71: 1552–1576

Corel et al (1998). Cytotoxic T cell and neutralizing antibody responses to human immunodeficiency virus type I envelope with a combination vaccine regimen. J Inf Dis 177:301–309

Cox I C and Coulter A R (1997). Adjuvants—a classification and review of their modes of action. Vaccine 15:248–256 1 6

Donnelly J J, Ulmer J B, Shiver J W & Liu M A (1997). DNA vaccines. Annu Rev Immunol 15: 617–648

Falo L D Jr, & Storkus W J (I 998). Giving DNA vaccines a helping hand. Nature Medicine 4(ii): 1236–1240 FASEB J December 12 15: 1611–26

Fomsgaard A (1999). HIV-I DNA vaccines. Immunol Lett. January;65(1–2):127–31.

Forster R, Mattis A E, Kremmer E, Wolf E, Brem G, Lipp M (1996). A putative chemokine receptor, BLRI, directs B cell migration to defined lymphoid organs and specific anatomic compartments of the spleen. Cell December 13 87(6): 1037–47

Foxman E F, Campbell J J, Butcher E C (1997). Multistep navigation and the combinatorial control of leukocyte chemotaxis. J Cell Biol December 1 139:5 1349–60

Gunn M D, Ngo V N, Ansel K M, Ekland E H, Cyster J O, Williams L T (1998). A B-cell-homing chemokine made in lymphoid follicles activates Burkitt's lymphoma receptor-I. Nature February 19 391:6669 799–803

Gupter R K and Siber G R (1995). Adjuvants for human vaccines—current status, problems and future prospects. Vaccine 13:1263–1276

Kennedy R C (1997). DNA vaccination for HIV. Nat Med May 3:5 501–2

Kim C H and Broxmeyer H E (1998). In vitro behavior of hematopoietic progenitor cells under the influence of chemoattractants: SDF-1, steel factor and the bone marrow environment. Blood 91:100–1 10

Kim C H and Broxmeyer H E (1999). Chemokines: Signal lamps for trafficking of T and B cells for development and effector function. J Leukocyte Biol. 65(i):6–15

Kim C H, et al (I 999). Chemokines: signal lamps for trafficking of T and B cells for development and effector function. J Leukoc Biol. Jan;65(1):6–15

Kim I J, Nottingham L K, Sin Ji, Tsai A, Morrison L, Oh J. Dang K, Hu Y, Kazahaya K, Bennet M, Dentchev T, Wilson D M, Chalian C C, Boyer J D, Agadjanyan M G, and Weiner D B (1998). CDS positive T cells influence antigen-specific immune responses through the expression of chemokines. J Clin Invest 102(6): 1112–1124

Legier D F, Loetscher M, Roos R S, Lewis C, Baggiolini M, Moser M (1998). B cell-attracting chemokine 1, a human CXC chemokine expressed in lymphoid tissues, selectively attracts B lymphocytes via BLRI/CXCRS. J Exp Med 187: 655–660

Mackay C R (1997). Chemokines: what chemokine is that? Curr Biol 7: R384–R386

Miyahira Y, Murata K, Rodriguez D, Rodriguez J R, Esteban M, Rodrigues M M, Zavala F (1995). Quantification of antigen specific CD8+T cells using an ELISPOT assay. J Immunol Methods 1995 April 12 181(t): 45–54.

Moelling K (I 997). Naked DNA for vaccine and therapy. J Mol Med 75:242–246

Montgomery D L, Ulmer J E, Donnelly J J and Liu M A (I 997). DNA vaccines. Phumacol Ther 74(2): 195–205)

Mor G, Singla M, Steinberg A D, Hoffman S L, Okuda K, Klinman D M (1997).Do DNA vaccines induce autoimmune disease? Hum Gene Ther February 10 8:3 293–300

Moser B, et a) (I 998). Lymphocyte responses to chemokines.Int Rev Immunol. 16(3–4):323–44.

Nelson P J & Krensky E M (1998). Chemokines, lymphocytes and viruses: what goes around comes around. Curr Opin Immunol 10: 265–270

Okada E, Sasaki S, Ishii N, Aoki 1, Yasuda T, Nishioka K, Fukushima J, Wahren B and Okuda K (I 997). Intranasal immunization of a DNA vaccine with Interieukin 12 and Granulocyte macrophage colony stimulating factor expressing plasmids in liposomes induce strong mucosal and cell-mediated immune responses against HIV-1 antigen. J Immunol 159: 3638–3647

Oppenheinn J, et al (I 996). The role of cytokines in cancer. Cytokine Growth Factor Rev. October; 7(3):279–8 8.

Richmond J F L, Lu S, Santoro J C, Weng J, Hu S-L, Montefiori D C and Robinson H L (1998). Studies of the neutralizing activity and avidity of anti-human immunodeficiency virus type I Env antibody elicited by DNA priming and protein boosting. J Virol. 72(11):9097–9100

Ruiz P J, Garren H, Ruiz I U, Hirschberg D L, Nguyen L V, Karpuj M V, Cooper M T, Mitchell D J, Fathman C G, Steinman L (1999). Suppressive immunization with DNA encoding a self-peptide prevents autoimmune disease: modulation of T cell costimulation. J Immunol Mar 15; 162(6):3336–41

Sasaki S, Tsuji T, Asakura Y, Fukushima J and Okuda K (1998). 'Be search for a potent DNA vaccine against AIDS: Ile enhancement of immunogenicity by chemical and genetic adjuvants. Anticancer Res 18:3907–3916

Sha Z, et al (1999). Enhancement of mucosal immune responses to the influenza virus HA protein by alternative approaches to DNA immunization. Inununobiology. February; 200(i):21–30.

Sheikh N A, et al. (1999). Generation of antigen specific CD8+ cytotoxic T cells following immunization with soluble protein formulated with novel glycoside adjuvants. Vaccine. Aug. 6, 1999; 17(23–24):2974–82

Simons G, Clapham P R, Picard L, Offord R E, Rosankilde N N, Schwartz T W, Buser R, Wells T N C and Proudfoot A E (1997). Potent inhibition of HIV-1 infectivity in macrophages and lymphocytes by a novel CCR5 antagonist. Sciences 267:267–279

Sin 11, et al (1999). IL-12 gene as a DNA vaccine adjuvant in a herpes mouse model: IL-12 enhances Thi-type CD4+ T cell-mediated protective immunity against herpes simplex virus-2 challenge. J Immunol. March 1; 1 62(5) :2912–21

Street N E and Moosmann T R (1991). Functional diversity of T lymphocytes due to secretion of different cytokine patterns. FASEB J February 5(2):171–177

Struyf S, Proost P, Sozzani S, Mantovani A, Wuyts A, De Clercq E, Schols D, Van Damme J (1998). Enhanced anti-HIV-1 activity and altered chemotactic potency of N-H2-terminally processed macrophage-derived chemokine (NIDC) imply an additional MDC receptor. J Immunol September 15; 161(6):2672–5

Tang, D., M. DeVit, and S. Johnston (1992). Genetic immunization is a simple method for eliciting an immune response. Nature. 356: 152–154

Taub D D (I 996). Chemokine-leukoWe interactions. The voodoo that they do so well. Cytokine Growth Factor Rev 7:355–376

Toes R E, Blom R J, Offr-inga R, Kast W M, Melief C J (I 996). Enhanced tumor outgrowth after peptide vaccination. Functional deletion of tumor-specific CTL induced by peptide vaccination can lead to the inability to reject tumors. J Immunol May 15 156:10 3911–8

Ulmer, J. B., J. Donnelly, S. E. Parker, G. H. Rhodes, P. L. Felgner, V. L. Dwairki, S. H. Gromkowski, R. Deck, C. M. DeVitt, A. Friedman, et al (1993). Heterologous protection against influenza by injection of DNA encoding a viral protein. Science. 259: 1745–1749

VanCott T C et al (1997). Antibodies with specificity to native gp120 and neutralization activity against primary human immunodeficiency virus type I isolates elicited by immunization with oligomeric gp 1 20. J Virol 71: 4319–4330

VaxGen (1999). Thai authorities approves large-scale testing of VaxGen's HIV vaccine (AIDSVAX); Trial focused on HIV Epidemic in Asia and Pacific Rim.

Wang, B, Ugen, K E, Srikantan, V, Agadjanyan, M G, Dang, K, Refaeli, Y, Sato, A, Boyer, J Williams, W N and Weiner D B (1993). Gene inoculation generates immune responses against human immunodeficiency virus type 1. Proc. Natl. Acad. Sci. USA. 90: 4156–4160

Wang, B-, K. E. Ugen, V. Srikantan, M. G. Agadjanyan, K. Dang, Y. Refaeli, A. Sato, J. Boyer, W. V. Williams, and D. B. Weiner (1993). Gene inoculation generates immune responses against human immunodeficiency virus type 1. Proc. Nati. Acad. Sci. USA. 90: 4156–4160

Ward S G, Bacon K, Westwick J (I 998). Chemokines and T lymphocytes: more than an attraction. Immunity July 9 1: 1–11I Wolff J A, Malone R W, Williams P, Chong W, Acsadi G, Jani A, Felgner P L (I 990). Direct gene transfer into mouse muscle in vivo. Science March 23 247, 4949 Pt 1: 1465–8

Wu L, Paxton W A, Kassam N et al. (I 997). CCR5 levels and expression pattern correlate with infectability by macrophage-tropic HIV-1, in vitro. J Exp Med 185(9): 1681–91

Xin K Q, et al (1999). Immunization of RANTES expression plasmid with a DNA vaccine enhances HIV-1-specific immunity. Clin Immunol. July 92(l):90–6

Xin K-Q, Lu Y, Hamajima K, FukushimaJ, Yang J, Inamura K and Okuda K (1999). Immunization of RANTES expression plasmid with DNA vaccine enhances HIV-1-specific immunity. Clin. Immunol. 92(i): 90–96

Yoshimura T, Robinson E A, Tanaka S et al (1989). Purification and amino-acid analysis of two human glioma-derived monocyte chemoattractants. I Exp Med 169: 1449–59

What is claimed is:

1. A composition comprising:
an isolated HIV antigen against which an immune response is desired in a subject wherein the HIV antigen is selected from the group consisting of gp120 and gp160;
a chemokine, wherein the chemokine is macrophage-derived chemokine (MDC) consisting of SEQ ID. NO. 2; and
a pharmaceutically acceptable carrier.

2. The composition of claim 1, further comprising one or more components selected from the group consisting of: pharmaceutically acceptable excipients, adjuvants, wetting agents; emulsifying agents, and pH buffering agents.

3. A composition comprising:
(1) an isolated HIV antigen against which an immune response is desired in a subject wherein the HIV antigen is selected from the group consisting of gp120 and gp160;
(2) macrophage-derived chemokine (MDC); and
(3) a pharmaceutically acceptable carrier.

4. A method for enhancing the efficacy of an immune response against an HIV antigen in a subject comprising administering to the subject the composition of claim 1.

5. A method to achieve an improvement in a subject's immune response to an HIV antigen, the method comprising:
administering to the subject a composition comprising:
an isolated HIV antigen against which an immune response is desired in the subject wherein the HIV antigen is selected from the group consisting of $gp^{120}$ and gp160;
a chemokine, wherein the chemokine is macrophage-derived chemokine (MDC); and
a pharmaceutically acceptable carrier.

6. The method of claim 5 wherein the subject is a human.

* * * * *

SEQUENCE LISTING

<160> NUMBER OF SEQ ID NOS: 7

<210> SEQ ID NO 1
<211> LENGTH: 2923
<212> TYPE: DNA
<213> ORGANISM: Homo sapiens

<400> SEQUENCE: 1

```
gagacataca ggacagagca tggctcgcct acagactgca ctcctggttg tcctcgtcct      60
ccttgctgtg gcgcttcaag caactgaggc aggcccctac ggcgccaaca tggaagacag     120
cgtctgctgc cgtgattacg tccgttaccg tctgccctg cgcgtggtga aacacttcta     180
ctggacctca gactcctgcc cgaggcctgg cgtggtgttg ctaaccttca gggataagga     240
gatctgtgcc gatcccagag tgccctgggt gaagatgatt ctcaataagc tgagccaatg     300
aagagcctac tctgatgacc gtggccttgg ctcctccagg aaggctcagg agccctacct     360
ccctgccatt atagctgctc cccgccagaa gcctgtgcca actctctgca ttccctgatc     420
tccatccctg tggctgtcac ccttggtcac ctccgtgctg tcactgccat ctcccccctg     480 accctctaa cccatcctct gcctcctcc ctgcagtcag agggtcctgt tcccatcagc     540
gattcccctg cttaaaccct tccatgactc cccactgccc taagctgagg tcagtctccc     600
aagcctggca tgtggccctc tggatctggg ttccatctct gtctccagcc tgcccacttc     660
ccttcatgaa tgttgggttc tagctccctg ttctccaaac ccatactaca catcccactt     720
ctgggtcttt gcctgggatg ttgctgacac tcagaaagtc ccaccacctg cacatgtgta     780
gccccaccag ccctccaagg cattgctcgc ccaagcagct ggtaattcca tttcatgtat     840
tagatgtccc ctggccctct gtcccctctt aataacccta gtcacagtct ccgcagattc     900
ttgggatttg ggggttttct cccccacctc tccactagtt ggaccaaggt ttctagctaa     960
gttactctag tctccaagcc tctagcatag agcactgcag acaggccctg gctcagaatc    1020
```

```
agagcccaga aagtggctgc agacaaaatc aataaaacta atgtccctcc cctctccctg    1080
ccaaaaggca gttacatatc aatacagaga ctcaaggtca ctagaaatgg ccagctggg    1140 tcaatgtgaa gccccaaatt tgcccagatt cacctttctt ccccactcc cttttttttt    1200 tttttttttt tgagatggag tttcgctctt gtcacccacg ctggagtgca atggtgtggt    1260
cttggcttat tgaagcctct gcctcctggg ttcaagtgat tctcttgcct cagcctcctg    1320
agtagctggg attacaggtt cctgctacca cgcccagcta attttttgtat tttagtaga    1380 gacgaggctt caccatgttg gccaggctgg tctcgaactc ctgtcctcag gtaatccgcc    1440
cacctcagcc tcccaaagtg ctgggattac aggcgtgagc cacagtgcct ggcctcttcc    1500
ctctccccac tgccccccc aacttttttt ttttttttat ggcagggtct cactctgtcg    1560
cccaggctgg agtgcagtgg cgtgatctcg gctcactaca acctcgacct cctgggttca    1620
agtgattctc ccaccccagc ctcccaagta gctgggatta caggtgtgtg ccactacggc    1680
tggctaattt ttgtattttt agtagagaca ggtttcacca tattggccag ctggtcttg    1740 aactcctgac ctcaagtgat ccaccttcct tgtgctccca aagtgctgag attacaggcg    1800
tgagctatca cacccagcct ccccttttt ttcctaatag gagactcctg taccttcett    1860 cgttttacct atgtgtcgtg tctgcttaca tttccttctc ccctcaggct tttttgggt    1920 ggtcctccaa cctccaatac ccaggcctgg cctcttcaga gtaccccca ttccactttc    1980 cctgcctcct tccttaaata gctgacaatc aaattcatgc tatggtgtga agactacct    2040 ttgacttggt attataagct ggagttatat atgtatttga aaacagagta aatacttaag    2100
aggccaaata gatgaatgga agaattttag gaactgtgag aggggacaa ggtgaagctt    2160 tcctggccct gggaggaagc tggctgtggt agcgtagcgc tctctctctc tgtctgtggc    2220
aggagccaaa gagtagggtg taattgagtg aaggaatcct gggtagagac cattctcagg    2280
tggttgggcc aggctaaaga ctgggagttg ggtctatcta tgcctttctg gctgattttt    2340
gtagagacgg ggttttgcca tgttacccag gctggtctca aactcctggg ctcaagcgat    2400
cctcctggct cagcctccca agtgctggga ttacaggcg tgaatcactg cgcctggctt    2460
cctcttcctc ttgagaaata ttctttcat acagcaagta tgggacagca gtgtcccagg    2520
taaaggacat aaatgttaca agtgtctggt cctttctgag ggaggctggt gccgctctgc    2580
agggtatttg aacctgtgga attggaggag gccatttcac tccctgaacc cagcctgaca    2640
aatcacagtg agaatgttca ccttataggc ttgctgtggg gctcaggttg aaagtgtggg    2700
gagtgacact gcctaggcat ccagctcagt gtcatccagg gcctgtgtcc ctcccgaacc    2760
cagggtcaac ctgcctgcca caggcactag aaggacgaat ctgcctactg cccatgaacg    2820
gggccctcaa gcgtcctggg atctccttct ccctcctgtc ctgtccttgc ccctcaggac    2880
tgctggaaaa taaatccttt aaaatagtaa aaaaaaaaa aaa                       2923
```

<210> SEQ ID NO 2
<211> LENGTH: 93
<212> TYPE: PRT
<213> ORGANISM: Homo sapiens

<400> SEQUENCE: 2

Met Ala Arg Leu Gln Thr Ala Leu Leu Val Val Leu Val Leu Leu Ala
1               5                   10                  15

Val Ala Leu Gln Ala Thr Glu Ala Gly Pro Tyr Gly Ala Asn Met Glu
            20                  25                  30

```
Asp Ser Val Cys Cys Arg Asp Tyr Val Arg Tyr Arg Leu Pro Leu Arg
        35                  40                  45

Val Val Lys His Phe Tyr Trp Thr Ser Asp Ser Cys Pro Arg Pro Gly
 50                  55                  60

Val Val Leu Leu Thr Phe Arg Asp Lys Glu Ile Cys Ala Asp Pro Arg
65                  70                  75                  80

Val Pro Trp Val Lys Met Ile Leu Asn Lys Leu Ser Gln
                85                  90

<210> SEQ ID NO 3
<211> LENGTH: 725
<212> TYPE: DNA
<213> ORGANISM: Homo sapiens

<400> SEQUENCE: 3
ctaacccaga acatccaat tctcaaactg aagctcgcac tctcgcctcc agcatgaaag     60
tctctgccgc ccttctgtgc ctgctgctca tagcagccac cttcattccc caagggctcg    120
ctcagccaga tgcaatcaat gccccagtca cctgctgtta aacttcacc aataggaaga    180 tctcagtgca gaggctcgcg agctatagaa gaatcaccag cagcaagtgt cccaaagaag    240
ctgtgatctt caagaccatt gtggccaagg agatctgtgc tgaccccaag cagaagtggg    300
ttcaggattc catggaccac ctggacaagc aaacccaaac tccgaagact tgaacactca    360
ctccacaacc caagaatctg cagctaactt atttttcccct agctttcccc agacaccctg    420
ttttatttta ttataatgaa ttttgtttgt tgatgtgaaa cattatgcct taagtaatgt    480
taattcttat ttaagttatt gatgttttaa gtttatcttt catggtacta gtgttttttta    540 gatacagaga cttggggaaa ttgcttttcc tcttgaacca cagttctacc cctgggatgt    600
tttgagggtc tttgcaagaa tcattaatac aaagaatttt ttttaacatt ccaatgcatt    660
gctaaaatat tattgtggaa atgaatattt tgtaactatt acaccaaata aatatatttt    720
tgtac                                                                 725

<210> SEQ ID NO 4
<211> LENGTH: 276
<212> TYPE: DNA
<213> ORGANISM: Homo sapiens

<400> SEQUENCE: 4
atgaaggtct ccgcggcacg cctcgctgtc atcctcattg ttactgccct ctgcgctcct     60
gcatctgcct ccccatattc ctcggacacc acaccctgct gctttgccta cattgcccgc    120
ccactgcccc gtgcccacat caaggagtat ttctacacca gtggcaagtg ctccaaccca    180
gcagtcgtct ttgtcacccg aaagaaccgc caagtgtgtg ccaacccaga gaagaaatgg    240
gttcgggagt acatcaactc tttggagatg agctag                              276

<210> SEQ ID NO 5
<211> LENGTH: 663
<212> TYPE: DNA
<213> ORGANISM: Homo sapiens
<220> FEATURE:
<221> NAME/KEY: misc_feature
<222> LOCATION: (564)..(564)
<223> OTHER INFORMATION: n can be any one of a, c, t, and g.
<221> NAME/KEY: misc_feature
<222> LOCATION: (583)..(583)
<223> OTHER INFORMATION: n can be any one of a, c, t, and g.
<221> NAME/KEY: misc_feature
<222> LOCATION: (590)..(590)
<223> OTHER INFORMATION: n can be any one of a, c, t, and g.
```

```
<221> NAME/KEY: misc_feature
<222> LOCATION: (595)..(595)
<223> OTHER INFORMATION: n can be any one of a, c, t, and g.
<221> NAME/KEY: misc_feature
<222> LOCATION: (625)..(625)
<223> OTHER INFORMATION: n can be any one of a, c, t, and g.
<221> NAME/KEY: misc_feature
<222> LOCATION: (631)..(631)
<223> OTHER INFORMATION: n can be any one of a, c, t, and g.
<221> NAME/KEY: misc_feature
<222> LOCATION: (640)..(640)
<223> OTHER INFORMATION: n can be any one of a, c, t, and g.
<221> NAME/KEY: misc_feature
<222> LOCATION: (658)..(658)
<223> OTHER INFORMATION: n can be any one of a, c, g, and t.

<400> SEQUENCE: 5
cagagctcaa gtctgaactc tacctccaga cagaatgaag ttcatctcga catctctgct      60
tctcatgctg ctggtcagca gcctctctcc agtccaaggt gttctggagg tctattacac     120
aagcttgagg tgtagatgtg tccaagagag ctcagtcttt atccctagac gcttcattga     180
tcgaattcaa atcttgcccc gtgggaatgg ttgtccaaga aaagaaatca tagtctggaa     240
gaagaacaag tcaattgtgt gtgtggaccc tcaagctgaa tggatacaaa gaatgatgga     300
agtattgaga aaagaagtt cttcaactct accagttcca gtgtttaaga aaagattcc       360 ctgatgctga tatttccact aagaacacct gcattcttcc cttatccctg ctctgggatt     420
ttagttttgt gcttagttaa atcttttcca gggagaaaga acttccccat acaaataagg     480
catgaggact atgtaaaaat aaccttgcag gagctggatg gggggccaaa ctcaagcttc     540
tttcactcca caggcaccct attntacact tggggttttt gcnttctttn tttcntcagg     600 ggggggaaa gtttcttttg gaaantagtt nttccagttn ttaggtatta cagggttntt     660
ttt                                                                 663

<210> SEQ ID NO 6
<211> LENGTH: 19
<212> TYPE: PRT
<213> ORGANISM: Artificial Sequence
<220> FEATURE:
<223> OTHER INFORMATION: Truncated homo sapiens MDC peptide

<400> SEQUENCE: 6

Tyr Gly Ala Asn Met Glu Asp Ser Val Cys Cys Arg Asp Tyr Val Arg
1               5                   10                  15

Tyr Arg Leu

<210> SEQ ID NO 7
<211> LENGTH: 13
<212> TYPE: PRT
<213> ORGANISM: Artificial Sequence
<220> FEATURE:
<223> OTHER INFORMATION: Truncated homo sapiens MDC peptide

<400> SEQUENCE: 7

Pro Tyr Gly Ala Asn Met Glu Asp Ser Val Cys Cys Arg
1               5                   10
```